(12) United States Patent
Allen et al.

(10) Patent No.: US 7,141,692 B2
(45) Date of Patent: Nov. 28, 2006

(54) MOLECULAR PHOTORESISTS CONTAINING NONPOLYMERIC SILSESQUIOXANES

(75) Inventors: Robert David Allen, San Jose, CA (US); Wu-Song Huang, Poughkeepsie, NY (US); Mahmoud Khojasteh, Poughkeepsie, NY (US); Qinghuang Lin, Yorktown Heights, NY (US); Dirk Pfeiffer, Dobbs Ferry, NY (US); Ratnam Sooriyakumaran, San Jose, CA (US); Hoa D. Truong, San Jose, CA (US)

(73) Assignee: International Business Machines Corporation, Armonk, NY (US)

( * ) Notice: Subject to any disclaimer, the term of this patent is extended or adjusted under 35 U.S.C. 154(b) by 418 days.

(21) Appl. No.: 10/721,302

(22) Filed: Nov. 24, 2003

(65) Prior Publication Data

US 2005/0112382 A1    May 26, 2005

(51) Int. Cl.
C08G 77/14 (2006.01)

(52) U.S. Cl. ............... 556/460; 556/439; 556/425; 556/449; 430/270.1; 430/313; 430/323; 430/330; 430/331; 430/326; 430/905; 430/926

(58) Field of Classification Search ........... 556/460, 556/439, 425, 449; 430/926, 270.1, 313, 430/323, 330, 331, 326, 905
See application file for complete search history.

(56) References Cited

U.S. PATENT DOCUMENTS

| | | | |
|---|---|---|---|
| 5,047,492 A | 9/1991 | Weidner et al. | |
| 5,338,818 A | 8/1994 | Brunsvold et al. | |
| 5,385,804 A | 1/1995 | Premlatha et al. | |
| 5,484,867 A | 1/1996 | Lichtenhan et al. | |
| 5,723,257 A | 3/1998 | Iwasa | |
| 5,731,126 A * | 3/1998 | Takemura et al. | 430/270.1 |
| 5,942,638 A | 8/1999 | Lichtenhan et al. | |
| 6,087,064 A | 7/2000 | Lin et al. | |
| 6,100,417 A | 8/2000 | Lichtenhan et al. | |
| 6,197,473 B1 | 3/2001 | Kihara et al. | |
| 6,309,796 B1 * | 10/2001 | Nakashima et al. | 430/287.1 |
| 6,440,550 B1 | 8/2002 | Hacker | |
| 6,472,076 B1 | 10/2002 | Hacker | |
| 6,509,138 B1 | 1/2003 | Gleason et al. | |
| 6,623,909 B1 * | 9/2003 | Hatakeyama et al. | 430/270.1 |
| 6,632,582 B1 | 10/2003 | Kishimura et al. | |
| 2002/0013059 A1 * | 1/2002 | Kishimura et al. | 438/694 |
| 2002/0090572 A1 | 7/2002 | Sooriyakumaran et al. | |
| 2003/0065101 A1 | 4/2003 | Blakeney et al. | |
| 2003/0099899 A1 | 5/2003 | Gronbeck et al. | |
| 2003/0108812 A1 | 6/2003 | Rottstegge et al. | |

OTHER PUBLICATIONS

Fujita et al. (1996), "Nanometer-Scale Resolution of Calixarene Negative Resist in Electron Beam Lithography," *J. Vac. Sci. Technol.* B 14(6):4272-4276.
Kodama et al. (2002), "Synthesis of Novel Fluoropolymer for 157nm Photoresists by Cyclo-Polymerization," *Advances in Resist Technology and Processing XIX, Proceedings of SPIE* 4690:76-83.
Kunz et al. (2001), "Experimental VUV Absorbance Study of Fluorine-Functionalized Polystyrenes," *Advances in Resist Technology and Processing XVIII, Proceedings of SPIE* 4345:285-295.
Mantz et al. (1996), "Thermolysis of Polyhedral Oligomeric Silsesquioxane (POSS) Macromers and POSS-Siloxane Copolymers," *Chem. Mater.* 8(6):1250-1259.
Nakayama et al. (1997), "A Negative-Working Alkaline Developable Photoresist Based on Calix[4]resorcinarene, a Cross-Linker, and a Photoacid Generator," *Chemistry Letters*, pp. 265-266.
Ochiai et al. (1997), "High Resolution EB Lithography on Organic Resists: Molecular Size Effect," *Journal of Photopolymer Science and Technology* 10(4):641-646.
Toriumi et al. (2002), "Fluoropolymer Resists for 157-nm Lithography," *Advances in Resist Technology and Processing XIX, Proceedings of SPIE* 4690:191-199.
Yoshimura et al. (1997), "Effects of Molecular-Weight Distributions of Resist Polymers and Process Control on Lithography for 0.1 μm and Below," *Journal of Photopolymer Science and Technology* 10(4):629-634.

* cited by examiner

*Primary Examiner*—Margaret G. Moore
(74) *Attorney, Agent, or Firm*—Mintz Levin Cohn Ferris Glovsky and Popeo PC

(57) ABSTRACT

A nonpolymeric silsesquioxane is provided wherein at least one silicon atom of the silsesquioxane is directly or indirectly bound to an acid-cleavable substituent $R^{CL}$. The silsesquioxane has a glass transition temperature $T_g$ of greater than 50° C., and the $R^{CL}$ substituent can be cleaved from the silsesquioxane at a temperature below $T_g$, generally at least 5° C. below $T_g$. The remainder of the silicon atoms within the silsesquioxane structure may be bound to additional acid-cleavable groups, acid-inert polar groups $R^P$, and/or acid-inert nonpolar groups $R^{NP}$. The nonpolymeric silsesquioxane can be a polyhedral silsesquioxane optionally having one to three open vertices, such that the polyhedron appears to be a "partial cage" structure, or a macromer of two to four such polyhedral silsesquioxanes. Photoresist compositions containing the novel nonpolymeric silsesquioxanes are also provided, as is a method for using the compositions in preparing a patterned substrate.

69 Claims, No Drawings

MOLECULAR PHOTORESISTS CONTAINING NONPOLYMERIC SILSESQUIOXANES

TECHNICAL FIELD

This invention relates generally to the field of photolithography. More specifically, the invention relates to the use of nonpolymeric silsesquioxanes in lithographic photoresist compositions, particularly in chemical amplification photoresists.

BACKGROUND OF THE INVENTION

The patterning of radiation sensitive polymeric films with high energy radiation such as photons, electrons, or ion beams is the principle means of defining high resolution circuitry found in semiconductor devices. The radiation sensitive films, often referred to as photoresists regardless of the radiation source, generally consist of multicomponent formulations that are coated onto a desired substrate such as a silicon wafer. The radiation is most commonly ultraviolet light at wavelengths of 436, 365, 257, 248, 193 or 157 nanometers (nm), or a beam of electrons or ions, or 'soft' x-ray radiation, also referred to as extreme ultraviolet (EUV) or x-rays. The radiation is exposed pattern wise and induces a chemical transformation to occur that renders the solubility of the exposed regions of the films different from that of the unexposed areas when the films are treated with an appropriate developer, usually a dilute, basic aqueous solution, such as aqueous tetramethylammonium hydroxide (TMAH).

Typical photoresists contain a polymeric component and are generally comprised of a polymeric matrix, a radiation sensitive component, a casting solvent, and other performance enhancing additives. The highest performing photoresists in terms of sensitivity to radiation and resolution capability are "chemically amplified" photoresists, allowing high resolution, high contrast and high sensitivity that are not generally provided by other photoresists. Chemically amplified photoresists are based on a catalytic mechanism that allows a relatively large number of chemical events such as, for example, deprotection reactions in the case of positive photoresists or crosslinking reactions in the case of negative tone photoresists, to be brought about by the application of a relatively low dose of radiation that induces formation of the catalyst, often a strong acid.

The absorbance characteristics of the polymeric matrix also impacts the suitability of a given photoresist for exposure with particular radiation sources. The choice of a polymer must be carefully considered when designing a material for lithographic applications, particularly where such polymers are to provide a relatively transparent matrix for radiation-sensitive compounds such as photoacid generators (PAGs). Absorbance characteristics are important because the wavelength of radiation used in optical lithography is directly proportional to the ultimate resolution attainable with a photoresist. The desire for higher resolution has therefore led to to the use of shorter and shorter radiation wavelengths. For example, the phenolic polymers used for 248 nm imaging, namely derivatives of poly(4-hydroxystyrene)(PHS), are unsuitable for use with 193 nm radiation as the opacity of these PHS materials at 193 nm does not allow for sufficient radiation to create an appropriate image profile throughout the photoresist film thickness. As a result, the selection of particular materials is necessary for each wavelength of optical radiation used.

The dissolution characteristics of photoresist materials in a developer are also important considerations. The semiconductor industry has largely supported the use of TMAH as a developer for photoresists. PHS materials, e.g., tend to dissolve very uniformly in TMAH without swelling. Additionally, the rate at which the polymeric films dissolve can be tuned, for example, by the use of protecting groups and dissolution inhibitors in positive tone photoresists, and by effective crosslinking and other functionalization in negative tone photoresists. Uniform dissolution has been a difficult property to incorporate into new photoresist materials, however, especially those designed specifically for 193 nm imaging. The current polymer resists for 193 nm imaging, such as acrylic acid derivatives, cyclic olefins and alternating cyclic olefin-maleic anhydride-based materials, generally fall into this category of nonlinear dissolution. In fact, these materials often exhibit significant swelling during the initial stages of development, making the development of photoresists based on these materials difficult.

Alternative materials based on fluoroalcohols have been previously proposed as a means of providing aqueous base solubility. See, e.g., Ito et al. (2001), "Polymer Design for 157 nm Chemcially Amplified Resists," Proc. SPIE 4345: 273–284; Kunz et al. (2001), "Experimental VUV Absorbance Study of Fluorine-Functionalized Polystyrenes," Proc. SPIE 4345:285–295; and Bae et. al. (2001), "Rejuvination of 248 mn Resist Backbones for 157 nm Lithography," J. Photopolym. Sci. Tech. 14:613–620. Examples of such materials include norbornene hexafluoroalcohol, styrene hexafluoroalcohol and cyclohexyldodecylfluoro-alcohol-based polymers. While each of these platforms provides base-soluble materials, each has disadvantages for commercial high resolution photoresist applications. For example, the norbornene hexafluoroalcohol monomer requires special polymerization conditions, such as ring-opening polymerization, transition metal catalyzed addition polymerization, or alternating free-radical polymerization with a comonomer such as maleic anhydride. Thus, this monomer does not accommodate a large number of suitable comonomers—a desirable property which allows for a large degree of variation in composition, and thereby, materials properties. As well, the styrene hexafluoroalcohol-based polymers are not suitable for imaging with 193 nm radiation due to their opacity at this wavelength, as with other styrenic materials such as PHS. The cyclohexyldodecylfluoroalcohol acrylates also suffer from their high degree of synthetic complexity and high manufacturing expense.

Other photoresists based upon silsesquioxane polymers have also been developed. For example, in commonly assigned U.S. patent application Ser. No. 10/079,289, entitled "Substantially Transparent Aqueous Base Soluble Polymer System for Use in 157 nm Resist Applications," novel fluorocarbinol- and/or fluoroacid-functionalized silsesquioxane polymers suitable for use in lithographic photoresist compositions are described. Photoresists containing silsesquioxane polymers have also been previously described in U.S. Pat. No. 6,087,064 to Lin et al., U.S. Pat. No. 5,385,804 to Premlatha et al., U.S. Pat. No. 5,338,818 to Brunsvold et al., and U.S. Pat. No. 5,399,462 to Sachdev et al., which disclose the use of aryl or benzyl substituted polysilsesquioxanes in photoresists.

Despite the widespread use of polymeric photoresist materials, as the need for higher resolutions and minimum feature sizes increases, certain characteristics of polymeric resist materials may result in non-uniform pattern features. For example, the non-linear dissolution rates of some polymers, as well as the distribution of polymer chain lengths and chain entanglements, may lead to non-uniform feature dimensions and line edge roughness at very small feature sizes. In turn, such pattern variations may induce fluctuations in threshold voltages and line resistances, thereby degrading circuit performance.

In principle, the use of nonpolymeric materials as photoresists represents a potentially useful approach for avoiding the problems associated with polymeric materials. Since resists derived from single molecules would not contain mixtures of polymer chains of varying lengths, the dissolution characteristics and properties should be uniform. In addition, higher resolutions and decreased line edge roughness may be possible since single molecules have much smaller sizes than polymers and would not suffer from molecular chain entanglement.

Although few examples of nonpolymeric resist materials have been reported to date, the use of certain nonpolymeric materials has been disclosed. In U.S. Pat. No., 6,197,473 to Kihara et al., for example, the use of calixarenes, i.e., cyclic phenolic resins, is disclosed. Photoresists based on calixarenes have also been previously described in, e.g., Ochiai et al. (1997), "High Resolution EB Lithography on Organic resists: Molecular Size Effect," *J. Photopolymer Sci. and Tech.* 10(4):641–646; and Fujita et al. (1996), "Nanometer-Scale resolution of Calixarene Negative Resist in Electron Beam Lithography," *J. Vac. Sci. Techol.*, B14(6):4272–4276.

In U.S. Pat. No. 6,632,582 to Kishimura et al., a siloxane compound is disclosed in which certain substituents may be attached to the silicon atoms, such as an alkyl compound, an ester compound, an ether compound, a sulfone compound, a sulfonyl compound and an aromatic compound. The use of such compounds as resist materials, however, appears to be compromised by the low glass transition temperatures ($T_g$) of the materials such that the post-exposure bake temperatures would exceed the $T_g$.

Although improvements in photoresist technology and materials have been made, an ongoing need exists for new photoresist materials and compositions that can provide desirable characteristics for high resolution photoresist applications.

SUMMARY OF THE INVENTION

In one aspect of the invention, a nonpolymeric silsesquioxane is provided that is suitable for incorporation into a photoresist composition. The nonpolymeric silsesquioxane has a glass transition temperature $T_g$ of greater than 50° C., and at least one silicon atom of the silsesquioxane is directly or indirectly bound to an acid-cleavable substituent $R^{CL}$. The remainder of the silicon atoms within the silsesquioxane structure may be bound to additional acid-cleavable groups, acid-inert polar groups $R^P$, and/or acid-inert nonpolar groups $R^{NP}$. $R^{CL}$ is preferably a relatively reactive group, such that the process of cleaving $R^{CL}$ from the silsesquioxane has a fairly low activation energy. In this way, following exposure of the silsesquioxane to acid, e.g., a photogenerated acid, $R^{CL}$ can be cleaved from the silsesquioxane at a temperature that is below $T_g$, typically at least 5° C. below $T_g$. The $T_g$ of the silsesquioxane can be increased by substituting one or more silicon atoms with bulky substituents such as bicyclic and polycyclic groups, which, in turn, increase the resolution of images provided using lithographic photoresist compositions containing a silsesquioxane of the invention. The nonpolymeric silsesquioxane can be a polyhedral silsesquioxane optionally having one to three open vertices (such that the polyhedron appears to be a "partial cage" structure) or a macromer of two to four such polyhedral silsesquioxanes, which may be the same or different. The polyhedral silsesquioxanes in the macromer may be joined directly or through a spacer, such as O, $CH_2$, $SO_2$, and $C_6H_{10}$. The size of these molecules is generally in the range of about 0.5 to about 1.5 nm.

In another aspect of the invention, positive tone photoresist compositions are provided containing a photoacid generator, or "PAG," in addition to the nonpolymeric silsesquioxane. These compositions may additionally contain other components, e.g., a dissolution-modifying additive such as a dissolution inhibitor. These photoresist compositions are useful in a process for patterning a substrate by: (a) coating a substrate with a photoresist composition comprised of (i) a nonpolymeric silsesquioxane in which at least one silicon atom is bound to an acid-cleavable substituent $R^{CL}$, wherein the silsesquioxane has a glass transition temperature $T_g$ of greater than 50° C., and (ii) a photoacid generator, to form a film; (b) pattern wise exposing the film to an imaging radiation source so as to form a latent, patterned image in the film; (c) baking the exposed film at a post-exposure bake temperature below $T_g$; and (d) developing the latent image with a developer to form a patterned substrate, i.e., to reveal a patterned resist image on the substrate. The developer is selected so as to render the exposed regions of the film soluble. The surface of the substrate which is coated with the photoresist may be a of semiconductor, ceramic, metallic, or organic material (e.g., an organic dielectric material or an organic underlayer of a bilayer resist). Exposure may be carried out using electron-beam, x-ray, or ultraviolet radiation, although radiation in the DUV and EUV, including 248 nm, 193 nm, 157 nm, and 13.4 nm, is preferred.

The patterned resist image may then be transferred to the underlying surface by etching into the surface through spaces in the patterned resist structure. In this way, the resist compositions of the invention can be used to create patterned material structures such as metal wiring lines, holes for contacts or vias, insulation sections (e.g., damascene trenches or shallow trench isolation means), trenches for capacitor structures, etc., as might be used in the design of integrated circuit devices. Etching is generally carried out using a reactive ion etching (RIE) process.

DETAILED DESCRIPTION OF THE INVENTION

I. Definitions and Nomenclature

Unless otherwise indicated, this invention is not limited to specific compositions, components, or process steps. It should also be noted that the singular forms "a" and "the" are intended to encompass plural referents, unless the context clearly dictates otherwise. The terminology used herein is for the purpose of describing particular embodiments only and is not intended to be limiting.

In this specification and in the claims that follow, reference will be made to a number of terms, which shall be defined to have the following meanings:

As used herein, the phrase "having the formula" or "having the structure" is not intended to be limiting and is used in the same way that the term "comprising" is commonly used.

The term "alkyl" as used herein refers to a linear or branched, saturated hydrocarbon substituent that generally, although not necessarily, contains 1 to about 24 carbon atoms, such as methyl, ethyl, n-propyl, isopropyl, n-butyl, isobutyl, t-butyl, octyl, decyl, tetradecyl, hexadecyl, eicosyl, tetracosyl, and the like. Generally, although again not necessarily, alkyl groups herein contain 1 to about 12 carbon atoms. The term "lower alkyl" intends an alkyl group of 1 to 6 carbon atoms, and the term "cycloalkyl" intends a cyclic alkyl group, typically having 3 to 12, preferably 3 to 8, carbon atoms. The term "substituted alkyl" refers to alkyl substituted with one or more substituent groups, i.e., wherein a hydrogen atom is replaced with a non-hydrogen substituent group, and the terms "heteroatom-containing alkyl" and "heteroalkyl" refer to alkyl substituents in which at least one carbon atom is replaced with a heteroatom such as O, N, or S. If not otherwise indicated, the terms "alkyl" and "lower alkyl" include linear, branched, cyclic, unsubstituted, substituted, and/or heteroatom-containing alkyl and lower alkyl, respectively.

The term "alkylene" as used herein refers to a difunctional linear or branched saturated hydrocarbon linkage, typically although not necessarily containing 1 to about 24 carbon atoms, such as methylene, ethylene, n-propylene, n-butylene, n-hexylene, decylene, tetradecylene, hexadecylene, and the like. Preferred alkylene linkages contain 1 to about 12 carbon atoms, and the term "lower alkylene" refers to an alkylene linkage of 1 to 6 carbon atoms, preferably 1 to 4 carbon atoms. The term "substituted alkylene" refers to an alkylene linkage substituted with one or more substituent groups, i.e., wherein a hydrogen atom is replaced with a non-hydrogen substituent group, and the terms "heteroatom-containing alkylene" and "heteroalkylene" refer to alkylene linkages in which at least one carbon atom is replaced with a heteroatom. If not otherwise indicated, the terms "alkylene" and "lower alkylene" include linear, branched, cyclic, unsubstituted, substituted, and/or heteroatom-containing alkylene and lower alkylene, respectively.

The term "alkoxy" as used herein refers to a group —O-alkyl wherein "alkyl" is as defined above.

The term "aryl" as used herein, and unless otherwise specified, refers to an aromatic substituent containing a single aromatic ring or multiple aromatic rings that are fused together (such that at least two atoms of one aromatic ring are shared by another aromatic ring), directly linked (such that a direct covalent bond links one atom of an aromatic ring to an atom in a second aromatic ring), or indirectly linked (such that the different aromatic rings are bound to a common group such as a methylene or ethylene moiety). Preferred aryl groups contain 5 to 24 carbon atoms and either one aromatic ring or 2 to 4 fused or linked aromatic rings, e.g., phenyl, naphthyl, biphenyl, and the like, with more preferred aryl groups containing 1 to 3 aromatic rings, and particularly preferred aryl groups containing 1 or 2 aromatic rings and 5 to 18, optimally 5 to 14, carbon atoms. "Substituted aryl" refers to an aryl moiety substituted with one or more substituent groups, and the terms "heteroatom-containing aryl" and "heteroaryl" refer to an aryl group in which at least one ring carbon atom is replaced with a heteroatom. Unless otherwise indicated, the term "aryl" includes substituted and/or heteroaryl species.

The term "arylene" as used herein refers to an aromatic linkage defined as for "aryl" substituents above, but wherein the aryl moiety is bifunctional instead of monofunctional. Unless otherwise indicated, the term "arylene" includes substituted and/or heteroarylene species.

The term "aralkyl" refers to an alkyl group with an aryl substituent, and the term "alkaryl" refers to an aryl group with an alkyl substituent, wherein "alkyl" and "aryl" are as defined above. In general, aralkyl and alkaryl groups herein contain 6 to 24 carbon atoms, while preferred aralkyl and alkaryl groups contain 6 to 18 carbon atoms, and particularly preferred such groups contain 6 to 14 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-dienyl, and the like. The terms "aralkylene" and "alkarylene" refer to an alkylene linkage with an aryl substituent and an arylene linkage with an alkyl substituent, and are otherwise defined as for "aralkyl" and "alkaryl."

The term "alicyclic" is used to refer to cyclic, non-aromatic compounds, substituents and linkages, e.g., cycloalkanes and cycloalkenes, cycloalkyl and cycloalkenyl substituents, and cycloalkylene and cycloalkenylene linkages. Often, the term refers to polycyclic compounds, substituents, and linkages, including bridged bicyclic, compounds, substituents, and linkages. Preferred alicyclic moieties herein contain 3 to about 30, typically 5 to about 14, carbon atoms. Unless otherwise indicated, the term "alicyclic" includes substituted and/or heteroatom-containing such moieties. It will be appreciated that the term "cyclic," as used herein, thus includes "alicyclic" moieties.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. Examples of heteroalkyl groups include alkoxyalkyl, alkoxyaryl, alkylsulfanyl-substituted alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

Unless otherwise indicated, the term "hydrocarbyl" is to be interpreted as including substituted and/or heteroatom-containing hydrocarbyl moieties. "Hydrocarbyl" refers to univalent hydrocarbyl radicals containing 1 to about 30 carbon atoms, preferably 1 to about 18 carbon atoms, most preferably 1 to about 12 carbon atoms, including linear, branched, cyclic, alicyclic, and aromatic species. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom.

By "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with a non-hydrogen substituent. Examples of suitable substituents herein include halo, hydroxyl, sulfhydryl, $C_1$–$C_{12}$ alkoxy, $C_5$–$C_{18}$ aryloxy, acyl (including $C_2$–$C_{12}$ alkylcarbonyl (—CO-alkyl) and $C_6$–$C_{18}$ arylcarbonyl (—CO-aryl)), acyloxy (—O-acyl), $C_2$–$C_{12}$ alkoxycarbonyl (—(CO)—O-alkyl), $C_6$–$C_{18}$ aryloxycarbonyl (—(CO)—O-aryl), $C_2$–$C_{12}$ alkylcarbonato (—O—(CO)—O-alkyl), $C_6$–$C_{18}$ arylcarbonato (—O—(CO)—O- aryl), carboxy (—COOH), carbamoyl (—(CO)—NH$_2$), mono-substituted $C_1$–$C_{12}$ alkylcarbamoyl (—(CO)—NH ($C_1$–$C_{12}$ alkyl)), di-substituted alkylcarbamoyl (—(CO)—N ($C_1$–$C_{12}$ alkyl)$_2$), mono-substituted $C_5$–$C_{18}$ arylcarbamoyl (—(CO)—NH—$C_5$–$C_{18}$ aryl), cyano (—C≡N), cyanato (—O—C≡N), formyl (—(CO)—H), amino (—NH$_2$), mono- and di-($C_1$–$C_{12}$ alkyl)-substituted amino, mono- and di-($C_5$–$C_{18}$ aryl)-substituted amino, $C_2$–$C_{12}$ alkylamido (—NH—(CO)-alkyl), $C_5$–$C_{18}$ arylamido (—NH—(CO)-aryl), imino (—CR=NH where R=hydrogen, $C_1$–$C_{12}$ alkyl, $C_5$–$C_{18}$ aryl $C_6$–$C_{18}$ alkaryl, $C_6$–$C_{18}$ aralkyl, etc.), alkylimino (—CR=N(alkyl), where R=hydrogen, alkyl, aryl, alkaryl, etc.), arylimino (—CR=N(aryl), where R=hydrogen, alkyl, aryl, alkaryl, etc.), $C_1$–$C_{20}$ alkylsulfanyl (—S-alkyl; also termed "alkylthio"), $C_5$–$C_{18}$ arylsulfanyl (—S-aryl; also termed "arylthio"), $C_1$–$C_{20}$ alkylsulfinyl (—(SO)-alkyl), $C_5$–$C_{18}$ arylsulfinyl (—(SO)-aryl), $C_1$–$C_{20}$ alkylsulfonyl (SO$_2$-alkyl), $C_5$–$C_{18}$ arylsulfonyl (—SO$_2$-aryl), phosphono (—P(O)(OH)$_2$), and the hydrocarbyl moieties $C_1$–$C_{24}$ alkyl (preferably $C_1$–$C_{12}$ alkyl), $C_5$–$C_{24}$ aryl (preferably $C_5$–$C_{18}$ aryl), and $C_6$–$C_{18}$ aralkyl. In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated. When the term "substituted" appears prior to a list of possible substituted groups, it is intended that the term apply to every member of that group. For example, the phrase "substituted alkyl and aryl" is to be interpreted as "substituted alkyl and aryl."

The term "fluorinated" refers to replacement of a hydrogen atom in a molecule or molecular segment with a fluorine atom, and includes perfluorinated moieties. The term "perfluorinated" is also used in its conventional sense to refer to a molecule or molecular segment wherein all hydrogen atoms are replaced with fluorine atoms. Thus, a "fluorinated" methyl group encompasses —CH$_2$F and —CHF$_2$ as well as the "perfluorinated" methyl group, i.e., —CF$_3$ (trifluoromethyl). The term "fluoroalkyl" refers to a fluorinated alkyl group, the term "fluoroalkylene" refers to a fluorinated alkylene linkage, the term "fluoroaryl" refers to a fluorinated aryl substituent, the term "fluoroarylene" refers to a fluorinated arylene linkage, the term "fluoroalicyclic" refers to a fluorinated alicyclic moiety, and the like.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The term "acid-cleavable" refers to a molecular segment containing at least one covalent bond that is cleaved upon exposure to acid. Typically, the reaction of acid-cleavable groups herein with photogenerated acid occurs only, or is promoted greatly by, the application of heat. Those skilled in the art will recognize the various factors that influence the rate and ultimate degree of cleavage of acid-cleavable groups as well as the issues surrounding integration of the cleavage step into a viable manufacturing process. The product of the cleavage reaction is generally an acidic group, which, when present in sufficient quantities, imparts solubility to the silsesquioxanes of the invention in basic aqueous solutions.

Analogously, the term "acid-inert" refers to a substituent that is not cleaved or otherwise chemically modified upon contact with photogenerated acid.

The terms "photogenerated acid" and "photoacid" are used interchangeably herein to refer to the acid that is created upon exposure of the present photoresist compositions to radiation, by virtue of the photoacid generator contained in the compositions.

The term "substantially transparent" as used to describe a polymer that is "substantially transparent" to radiation of a particular wavelength refers to a polymer that has an absorbance of less than about 5.0/micron, preferably less than about 3.0/micron, most preferably less than about 1.5/micron, at a selected wavelength.

The term "nonpolymeric" as applied to silsesquioxanes of the invention refers to a monomeric polyhedron that may have one to three open vertices (i.e., one to three missing Si and/or O atoms), and to a macromolecule of linked such polyhedra. In the latter case, the macromolecule is distinguishable from polymeric silsesquioxanes insofar as the nonpolymeric macromolecule of the invention is present in a population of identical macromolecules such that there is no molecular weight distribution as is seen with oligomers and polymers.

For additional information concerning terms used in the field of lithography and lithographic compositions, see *Introduction to Microlithography*, Eds. Thompson et al. (Washington, D.C.: American Chemical Society, 1994).

II. The Novel Silsesquioxanes

In general, the nonpolymeric silsesquioxanes of the invention contain at least one silicon atom that is bound to an acid-cleavable substituent $R^{CL}$, wherein the silsesquioxane has a glass transition temperature $T_g$ of greater than 50° C. and $R^{CL}$ is cleavable upon exposure to acid at a temperature that is at least 5° C. below $T_g$. In a preferred embodiment, $R^{CL}$ is cleavable upon exposure to acid at a temperature that is at least 10° C. below $T_g$.

In one aspect, the nonpolymeric silsesquioxanes are polyhedral silsesquioxanes optionally having one to three open vertices due to missing silicon or oxygen atoms. In another aspect, the nonpolymeric silsesquioxanes are macromers of two to four polyhedral silsesquioxanes that may be the same or different, with each polyhedral silsesquioxane optionally having one to three open vertices due to missing silicon or oxygen atoms. In such macromers, the silsesquioxane polyhedra are linked atom-to-atom rather than face-to-face, and may be linked either directly or through a spacer such as O, CH$_2$, SO$_2$, or C$_6$H$_{10}$. Preferred polyhedral silsesquioxanes have four to about ten polygonal faces.

Providing that at least one silicon atom of the nonpolymeric silsesquioxane is covalently bound to an acid-cleavable $R^{CL}$ moiety, as indicated above, each silicon atom of the nonpolymeric silsesquioxane is covalently bound to a moiety selected from: a hydrogen atom; an additional acid-cleavable moiety $R^{CL}$, wherein, if more than one $R^{CL}$ is present, they may be the same or different; an acid-inert, polar substituent $R^P$; and an acid-inert, nonpolar substituent $R^{NP}$. As with $R^{CL}$, if more than one acid-inert, polar substituent $R^P$ is present, and/or if more than one acid-inert, nonpolar substituent $R^{NP}$ is present, the various $R^P$ and/or $R^{NP}$ moieties may be the same or different. Thus, in addition to the at least one acid-cleavable substituent, the silsesquioxane may be substituted with at least one of $R^P$ and $R^{NP}$, i.e., (a) with $R^P$ and optionally $R^{NP}$ or (b) with $R^{NP}$ and optionally $R^P$.

A representative polyhedral silsesquioxane has the structure (PH—SSQ-1)

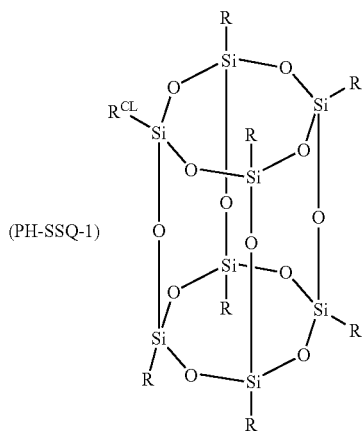

wherein the various R groups shown are H, $R^P$, $R^{NP}$, $R^{CL}$, or a combination thereof.

A representative polyhedral silsesquioxane with open verticles has the structure (PH—SSQ-2)

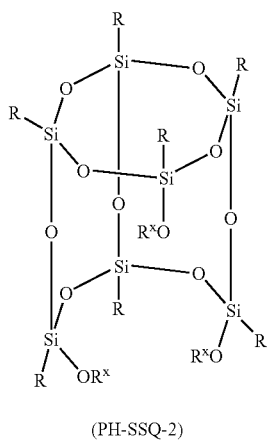

wherein R and $R^X$ may be H, an acid-cleavable group $R^{CL}$, an acid-inert polar substituent $R^P$, and/or an acid-inert nonpolar substituent $R^{NP}$, providing that at least one substituent is an acid-cleavable group.

The acid-cleavable substituent $R^{CL}$ generally, although not necessarily, has the structure of formula (I)

in which m, n, and q are independently zero or 1, r is an integer of at least 1 indicating the number of $-(L^2)_q-R^1$ present, and $L^1$, X, $L^2$, and $R^1$ are as follows:

$L^1$ is selected from $-O-SiR^2R^3-$, $C_1-C_{12}$ alkylene, substituted $C_1-C_{12}$ alkylene (e.g., $C_1-C_{12}$ fluoroalkylene or hydroxyl-substituted $C_1-C_{12}$ alkylene), $C_1-C_{12}$ heteroalkylene (e.g., $C_1-C_6$ alkoxy-substituted $C_1-C_6$ alkylene), substituted $C_1-C_{12}$ heteroalkylene (e.g., $C_1-C_6$ alkoxy- or hydroxyl-substituted $C_1-C_6$ fluoroalkylene), $C_5-C_{14}$ arylene, substituted $C_5-C_{14}$ arylene (e.g., $C_5-C_{14}$ fluoroarylene or hydroxyl-substituted $C_5-C_{14}$ arylene), $C_5-C_{14}$ heteroarylene (e.g., pyridinyl, pyrimidinyl, furanyl), substituted $C_5-C_{14}$ heteroarylene, $C_6-C_{14}$ aralkylene, substituted $C_6-C_{14}$ aralkylene, $C_6-C_{14}$ heteroaralkylene, and substituted $C_6-C_{14}$ heteroaralkylene, wherein $R^2$ and $R^3$ are hydrogen or $C_1-C_{12}$ hydrocarbyl, wherein when $L^1$ is optionally substituted and/or heteroatom-containing $C_3-C_{12}$ alkylene, $L^1$ may be linear, branched, or cyclic;

X is selected from $C_3-C_{30}$ alicyclic and substituted $C_3-C_{30}$ alicyclic;

$L^2$ is selected from $C_1-C_{12}$ alkylene, substituted $C_1-C_{12}$ alkylene, $C_1-C_{12}$ heteroalkylene, substituted $C_1-C_{12}$ heteroalkylene, $C_5-C_{14}$ arylene, substituted $C_5-C_{14}$ arylene, $C_5-C_{14}$ heteroarylene, substituted $C_5-C_{14}$ heteroarylene, $C_6-C_{14}$ aralkylene, substituted $C_6-C_{14}$ aralkylene, $C_6-C_{14}$ heteroaralkylene, and substituted $C_6-C_{14}$ heteroaralkylene, wherein when $L^2$ is optionally substituted and/or heteroatom-containing $C_3-C_{12}$ alkylene, $L^2$ may be linear, branched, or cyclic; and $R^1$ is selected from acid-cleavable ester, oligomeric ester, ether, carbonate, acetal, ketal, and orthoester substituents.

In preferred $R^{CL}$ substituents:

$L^1$ is $-O-SiR^2R^3-$ or $C_1-C_{12}$ alkylene, wherein $R^2$ and $R^3$ are as defined above. Preferably, $L^1$ is selected from $C_1-C_6$ alkylene and $-O-SiR^2R^3-$ in which $R^2$ and $R^3$ are $C_1-C_6$ alkyl. Such linkages include, by way of example, $-O-SiH(CH_3)-$, $-O-Si(CH_3)_2-$, $-O-SiH(CH_2CH_3)-$, $-O-SiH(C_6H_5)-$, $-CH_2-$, $-(CH_2)_2-$, $-(CH_2)_3-$, $-(CH_2)-CH(CH_3)-$, $-(CH_2)_2-CH(CH_2CH_3)$, $-CH_2-CH(CH_3)-CH_2-$, -Cy- wherein Cy is cyclohexyl, $-CH_2-Cy-CH_2-$, etc.

X is $C_3-C_{18}$ alicyclic, e.g., norbornanyl (NB), adamantanyl (AD), $-NB-CH_2-$, $-NB-(CH_2)_2-$, $-NB-(CH_2)_4-$, $-AD-CH_2-$, $-AD-(CH_2)_3-$, tetracyclododecyl (TD) etc. Generally, X is $C_3-C_{12}$ alicyclic.

$L^2$ is selected from $C_1-C_{12}$ alkylene, hydroxyl-substituted $C_1-C_{12}$ alkylene, $C_1-C_{12}$ fluoroalkylene, and hydroxyl-substituted $C_1-C_{12}$ fluoroalkylene, and in a particularly preferred embodiment is of the formula $-CR^{15}R^{16}-$ wherein $R^{15}$ is hydrogen, $C_1-C_{12}$ alkyl, or $C_1-C_{12}$ fluoroalkyl, and $R^{16}$ is $C_1-C_{12}$ alkyl or $C_1-C_{12}$ fluoroalkyl.

$R^1$ is selected from $-(CO)-O-R^4$, $-[Q^1-(CO)-O-]_h-R^5$, $-O-R^6$, and $-O-(CO)-O-R^7$ in which $R^4$, $R^5$, $R^6$, and $R^7$ are substituents that render $R^1$ cleavable from $R^{CL}$, and r is 1 or 2. The linkage $Q^1$ is $C_1-C_{12}$ alkylene or $C_1-C_{12}$ fluoroalkylene, and h is an integer in the range of 2 to 8 inclusive.

$R^4$ and $R^6$ are selected from (a) hydrocarbyl substituents with a tertiary carbon attachment point, (b) substituents having the structure $-CR^8R^9-O-CR^{10}R^{11}R^{12}$, and (c) substituents having the structure $-CR_{13}(OR^{14})_2$, wherein $R^5$, $R^7$, and $R^{14}$ are $C_4-C_{12}$ hydrocarbyl, substituted $C_4-C_{12}$ hydrocarbyl, heteroatom-containing $C_4-C_{12}$ hydrocarbyl, or substituted heteroatom-containing $C_4-C_{12}$ hydrocarbyl, and $R^8$, $R^9$, $R^{10}$, $R^{11}$, $R^{12}$, and $R^{13}$ are independently selected from hydrogen, $C_4-C_{12}$ hydrocarbyl, substituted $C_4-C_{12}$ hydrocarbyl, heteroatom-containing $C_4-C_{12}$ hydrocarbyl, and substituted heteroatom-containing $C_4-C_{12}$ hydrocarbyl, and further wherein any two of $R^8$, $R^9$, $R^{10}$, $R^{11}$, and $R^{12}$ may be linked to form a three- to eight-membered cyclic group.

It will be appreciated that when $R^4$ and $R^6$ have the structure $-CR^8R^9-O-CR^{10}R^{11}R^{12}$, then $R^1$ is an acetal or a ketal, since $R^1$ in this case is either $-(CO)-O-CR^8R^9-O-CR^{10}R^{11}R^{12}$ or $-O-CR^8R^9-O-CR^{10}R^{11}R^{12}$. Analogously, when $R^4$ and $R^6$ have the structure —$CR^{13}(OR^{14})_2$, then $R^1$ is an ortho ester substituent having the structure —(CO)—O—$CR^{13}(OR^{14})_2$ or —O—$CR^{13}(OR^{14})_2$. Examples of these $R^4$ and $R^6$ substituents include tetrahydropyranyl (THP), tetrahydrofuranyl (THF), 1-ethoxyethyl, 1-methoxy-cyclohexyl, and 1-methoxypropyl. When $R^4$ and $R^6$ are hydrocarbyl substituents having a tertiary carbon attachment point, these substituents may be either cyclic (including alicyclic) or acyclic. Such substituents include, without limitation, t-butyl, adamantyl, norbornyl, isobornyl, 2-methyl-2-adamantyl, 2-methyl-2-isobornyl, 2-methyl-2-tetracyclododecenyl, 2-methyl-2-dihydrodicyclo-pentadienyl-cyclohexyl, 1-methylcyclohexyl, and 1-methylcyclopentyl.

In a generally preferred embodiment, $R^1$ is of the formula —(CO)—O—$R^4$ and $L^2$ is —$CR^{15}R^{16}$—, such that $R^{CL}$ has the structure

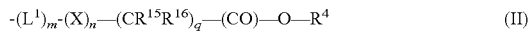  (II)

when r is 1. In another generally preferred embodiment, $R^1$ is of the formula —O—$R^6$ and $L^2$ is —$CR^{15}R^{16}$—, such that $R^{CL}$ has the structure

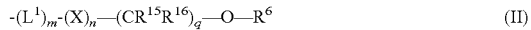  (II)

when r is 1. In these preferred structures, $R^4$ and $R^6$ are preferably acetals, ketals, or hydrocarbyl substituents with a tertiary carbon attachment point.

The polar substituent $R^P$ may be, for example, an anhydride, lactone, imide, fluoroalcohol, carboxylic acid, sulfonamide, or the like. Although not limited thereto, the polar substituent $R^P$ may have the structure (IV):

  (IV)

in which:

m1, n1, and q1 are independently zero or 1;

$L^3$ is defined as for $L^1$, i.e., $L^3$ is selected from —O—$SiR^{19}R^{20}$—, $C_1$–$C_{12}$ alkylene, substituted $C_1$–$C_{12}$ alkylene, $C_1$–$C_{12}$ heteroalkylene, substituted $C_1$–$C_{12}$ heteroalkylene, $C_5$–$C_{14}$ arylene, substituted $C_5$–$C_{14}$ arylene, $C_5$–$C_{14}$ heteroarylene, substituted $C_5$–$C_{14}$ heteroarylene, $C_6$–$C_{14}$ aralkylene, substituted $C_6$–$C_{14}$ aralkylene, $C_6$–$C_{14}$ heteroaralkylene, and substituted $C_6$–$C_{14}$ heteroaralkylene, wherein $R^{19}$ and $R^{20}$ are hydrogen or $C_1$–$C_{12}$ hydrocarbyl, and further wherein when $L^3$ is optionally substituted and/or heteroatom-containing $C_3$–$C_{12}$ alkylene, $L^1$ may be linear, branched, or cyclic;

Y is defined as for X, i.e., Y is selected from $C_3$–$C_{30}$ alicyclic and substituted $C_3$–$C_{30}$ alicyclic;

$L^4$ is defined as for $L^2$, i.e., $L^4$ is selected from $C_1$–$C_{12}$ alkylene, substituted $C_1$–$C_{12}$ alkylene, $C_1$–$C_{12}$ heteroalkylene, substituted $C_1$–$C_{12}$ heteroalkylene, $C_5$–$C_{14}$ arylene, substituted $C_5$–$C_{14}$ arylene, $C_5$–$C_{14}$ heteroarylene, substituted $C_5$–$C_{14}$ heteroarylene, $C_6$–$C_{14}$ aralkylene, substituted $C_6$–$C_{14}$ aralkylene, $C_6$–$C_{14}$ heteroaralkylene, and substituted $C_6$–$C_{14}$ heteroaralkylene, and further wherein when $L^4$ is optionally substituted and/or heteroatom-containing $C_3$–$C_{12}$ alkylene, $L^4$ may be linear, branched, or cyclic; and $R^{18}$ is an acid-inert, polar organic group containing a heteroatom with a Pauling electronegativity greater than about 3.00.

Preferred such acid-inert, polar substituents $R^P$ are those wherein:

$L^3$ is selected from —O—$SiR^{19}R^{20}$— and $C_1$–$C_{12}$ alkylene;

Y is $C_3$–$C_{18}$ alicyclic; and $L^4$ is selected from $C_1$–$C_{12}$ alkylene, hydroxyl-substituted $C_1$–$C_{12}$ alkylene, $C_1$–$C_{12}$ fluoroalkylene, and hydroxyl-substituted $C_1$–$C_{12}$ fluoroalkylene.

In particularly preferred $R^P$ substituents:

$L^3$ is selected from —O—$SiR^{19}R^{20}$— and $C_1$–$C_6$ alkylene;

Y is $C_6$–$C_{12}$ alicyclic; and $L^4$ is of the formula —$CR^{21}CR^{22}$— wherein $R^{21}$ is hydrogen, $C_1$–$C_{12}$ alkyl, or $C_1$–$C_{12}$ fluoroalkyl, and $R^{22}$ is $C_1$–$C_{12}$ alkyl or $C_1$–$C_{12}$ fluoroalkyl, such that $R^P$ has the structure -$(L^1)_{m1}$-$(Y)_{n1}$—$(CR^{21}R^{22})_{q1}$—$R^{18}$.

where m1, n1, q1 and $R^{18}$ are as defined above.

Preferably, the heteroatom of $R^{18}$ is O or N. Although not limited thereto, exemplary $R^{18}$ groups include hydroxyl, carboxyl, $C_1$–$C_{12}$ alkoxy, $C_1$–$C_{12}$ fluoroalkoxy, hydroxyl-substituted $C_1$–$C_{12}$ alkoxy, hydroxyl-substituted $C_1$–$C_{12}$ fluoroalkoxy, $C_2$–$C_{12}$ alkoxyalkyl, fluorinated $C_2$–$C_{12}$ alkoxyalkyl, hydroxyl-substituted $C_2$–$C_{12}$ alkoxyalkyl, fluorinated hydroxyl-substituted $C_2$–$C_{12}$ alkoxyalkyl, hydroxyl-substituted $C_1$–$C_{12}$ alkyl, hydroxyl-substituted $C_1$–$C_{12}$ fluoroalkyl, carboxyl-substituted $C_1$–$C_{12}$ alkyl, carboxyl-substituted $C_1$–$C_{12}$ fluoroalkyl, $C_2$–$C_{12}$ acyl, fluorinated $C_2$–$C_{12}$ acyl, hydroxyl-substituted $C_2$–$C_{12}$ acyl, fluorinated hydroxyl-substituted $C_2$–$C_{12}$ acyl, $C_2$–$C_{12}$ acyloxy, fluorinated $C_2$–$C_{12}$ acyloxy, hydroxyl-substituted $C_2$–$C_{12}$ acyloxy, fluorinated hydroxyl-substituted $C_2$–$C_{12}$ acyloxy, amino, mono- and di-($C_1$–$C_{12}$ alkyl)-substituted amino, amido, mono- and di-($C_2$–$C_{12}$ alkyl)amido, sulfonamido, N-heteroalicyclic, oxo-substituted N-heterocyclic, and, where the substituents permit, combinations of two or more of the foregoing.

In a particularly preferred aspect, $R^{18}$ is hydroxyl. It is also preferred that n1 is 1 and/or q1 is zero.

In another aspect, the silsesquioxane may contain at least one acid-inert, non-polar substituent $R^{NP}$. Exemplary such groups, without limitation, may be selected from $C_1$–$C_{18}$ hydrocarbyl and substituted $C_1$–$C_{18}$ hydrocarbyl, e.g., fluorinated $C_1$–$C_{18}$ hydrocarbyl. Acid-inert $R^{NP}$ moieties include, by way of example, $C_1$–$C_{18}$ alkyl, $C_1$–$C_{18}$ hydroxyalkyl, fluorinated $C_1$–$C_{18}$ alkyl, and fluorinated $C_1$–$C_{18}$ hydroxyalkyl. Examples of fluorinated hydroxyalkyl groups include, without limitation, fluorinated lower alkanol groups having the structure -$(L)_x$–$CQ^1Q^2$-OH, wherein x is zero or 1, L is a linker (e.g., $L^1$ or $L^2$ as defined earlier herein), $Q^1$ is F or $CF_3$, and $Q^2$ is H, F, or $CF_3$.

III. Photoresist Compositions

In another embodiment, a photoresist composition is provided that comprises both a nonpolymeric silsesquioxane, as described in detail above, and a photoacid generator, with the silsesquioxane representing up to about 99 wt. % of the solids included in the composition, and the photoacid generator representing approximately 0.1 to 25 wt. % of the solids contained in the composition. Other components and additives may also be present, e.g., dissolution modifying additives such as dissolution inhibitors.

The photoacid generator may be any compound that, upon exposure to radiation, generates a strong acid and is compatible with the other components of the photoresist composition. Examples of preferred photochemical acid generators (PAGs) include, but are not limited to, sulfonates, onium salts, aromatic diazonium salts, sulfonium salts, diaryliodonium salts and sulfonic acid esters of N-hydroxyamides or N-hydroxyimides, as disclosed in U.S. Pat. No. 4,731,605. Any PAG(s) incorporated into the present photoresists should have high thermal stability, i.e., stable to at least 140° C., so they are not degraded during pre-exposure processing.

Any suitable photoacid generator can be used in the photoresist compositions of the invention. Typical photoacid generators include, without limitation:

(1) sulfonium salts, such as triphenylsulfonium perfluoromethanesulfonate (triphenylsulfonium triflate), triphenylsulfonium perfluorobutanesulfonate, triphenylsulfonium perfluoropentanesulfonate, triphenylsulfonium perfluorooctanesulfonate, triphenylsulfonium hexafluoroantimonate, triphenylsulfonium hexafluoroarsenate, triphenylsulfonium hexafluorophosphate, triphenylsulfonium bromide, triphenylsulfonium chloride, triphenylsulfonium iodide, 2,4,6-trimethylphenyldiphenylsulfonium perfluorobutanesulfonate, 2,4,6-trimethylphenyldiphenylsulfonium benzenesulfonate, tris(t-butylphenyl)sulfonium perfluorooctane sulfonate, diphenylethylsulfonium chloride, and phenacyldimethylsulfonium chloride;

(2) halonium salts, particularly iodonium salts, including diphenyliodonium perfluoromethanesulfonate (diphenyliodonium triflate), diphenyliodonium perfluorobutanesulfonate, diphenyliodonium perfluoropentanesulfonate, diphenyliodonium perfluorooctanesulfonate, diphenyliodonium hexafluoroantimonate, diphenyliodonium hexafluoroarsenate, diphenyliodonium bis-(t-butylphenyl)iodonium triflate, and bis-(di-t-butylphenyl)-iodonium camphanylsulfonate;

(3) α,α'-bis-sulfonyl-diazomethanes such as bis(p-toluenesulfonyl)diazomethane, methylsulfonyl p-toluenesulfonyldiazomethane, 1-cyclohexylsulfonyl-1-(1,1-dimethylethylsulfonyl) diazomethane, and bis(cyclohexylsulfonyl) diazomethane;

(4) trifluoromethanesulfonate esters of imides and hydroxyimides, e.g., α-(trifluoromethylsulfonyloxy)-bicyclo[2.2.1]hept-5-ene-2,3-dicarboximide (MDT);

(5) nitrobenzyl sulfonate esters such as 2-nitrobenzyl p-toluenesulfonate, 2,6-dinitrobenzyl p-toluenesulfonate, and 2,4-dinitrobenzyl p-trifluoromethylbenzene sulfonate;

(6) sulfonyloxynaphthalimides such as N-camphorsulfonyloxynaphthalimide and N-pentafluorophenylsulfonyloxynaphthalimide;

(7) pyrogallol derivatives (e.g., trimesylate of pyrogallol);
(8) naphthoquinone-4-diazides;
(9) alkyl disulfones;
(10) s-triazine derivatives, as described in U.S. Pat. No. 4,189,323; and
(10) miscellaneous sulfonic acid generators including t-butylphenyl-α-(p-toluenesulfonyloxy)-acetate, t-butyl-α-(p-toluenesulfonyloxy)acetate, and N-hydroxy-naphthalimide dodecane sulfonate (DDSN), and benzoin tosylate.

Other suitable photoacid generators are disclosed in Reichmanis et al. (1991), *Chemistry of Materials* 3:395, and in U.S. Pat. No. 5,679,495 to Yamachika et al. Additional suitable acid generators useful in conjunction with the compositions and methods provided herein will be known to those skilled in the art and/or are described in the pertinent literature.

A dissolution modifying additive, generally although not necessarily a dissolution inhibitor, is typically included. If a dissolution inhibitor is present, it will typically represent in the range of about 1 wt. % to 40 wt. %, preferably about 5 wt. % to 30 wt. %, of the total solids.

Preferred dissolution inhibitors have high solubility in the resist composition and in the solvent used to prepare solutions of the resist composition (e.g., propylene glycol methyl ether acetate, or "PGMEA"), exhibit strong dissolution inhibition, have a high exposed dissolution rate, are substantially transparent at the wavelength of interest, may exhibit a moderating influence on $T_g$, strong etch resistance, and display good thermal stability (i.e., stability at temperatures of about 140° C. or greater). Suitable dissolution inhibitors include, but are not limited to, bisphenol A derivatives, e.g., wherein one or both hydroxyl moieties are converted to a t-butoxy substituent or a derivative thereof such as a t-butoxycarbonyl or t-butoxycarbonylmethyl group; fluorinated bisphenol A derivatives such as $CF_3$-bisphenol A-OCH$_2$(CO)—O-tBu (6F-bisphenol A protected with a t-butoxycarbonylmethyl group); normal or branched chain acetal groups such as 1-ethoxyethyl, 1-propoxyethyl, 1-n-butoxyethyl, 1-isobutoxy-ethyl, 1-t-butyloxyethyl, and 1-t-amyloxyethyl groups; and cyclic acetal groups such as tetrahydrofuranyl, tetrahydropyranyl, and 2-methoxytetrahydro-pyranyl groups; androstane-17-alkylcarboxylates and analogs thereof, wherein the 17-alkylcarboxylate at the 17-position is typically lower alkyl. Examples of such compounds include lower alkyl esters of cholic, ursocholic and lithocholic acid, including methyl cholate, methyl lithocholate, methyl ursocholate, t-butyl cholate, t-butyl lithocholate, t-butyl ursocholate, and the like (see, e.g., Allen et al. (1995) *J. Photopolym. Sci. Technol.*, cited supra); hydroxyl-substituted analogs of such compounds (ibid.); and androstane-17-alkylcarboxylates substituted with one to three 3 $C_1$–$C_4$ fluoroalkyl carbonyloxy substituents, such as t-butyl trifluoroacetyllithocholate (see, e.g., U.S. Pat. No. 5,580,694 to Allen et al.).

The remainder of the resist composition is composed of a solvent and may additionally, if necessary or desirable, include customary additives such as dyes, sensitizers, additives used as stabilizers and acid-diffusion controlling agents, coating aids such as surfactants or anti-foaming agents, adhesion promoters and plasticizers.

The choice of solvent is governed by many factors not limited to the solubility and miscibility of resist components, the coating process, and safety and environmental regulations. Additionally, inertness to other resist components is desirable. It is also desirable that the solvent possess the appropriate volatility to allow uniform coating of films yet also allow significant reduction or complete removal of residual solvent during the post-application bake process. See, e.g., *Introduction to Microlithography*, Eds. Thompson et al., cited previously. In addition to the above components, the photoresist compositions provided herein generally include a casting solvent to dissolve the other components so that the overall composition may be applied evenly on the substrate surface to provide a defect-free coating. Where the photoresist composition is used in a multilayer imaging process, the solvent used in the imaging layer photoresist is preferably not a solvent to the underlayer materials, otherwise the unwanted intermixing may occur. The invention is not limited to selection of any particular solvent. Suitable casting solvents may generally be chosen from ether-, ester-, hydroxyl-, and ketone-containing compounds, or mixtures of these compounds. Examples of appropriate solvents include carbon dioxide, cyclopentanone, cyclohexanone, ethyl 3-ethoxypropionate (EEP), a combination of EEP and γ-butyrolactone (GBL), lactate esters such as ethyl lactate, alkylene glycol alkyl ether esters such as PGMEA, alkylene glycol monoalkyl esters such as methyl cellosolve, butyl acetate, and 2-ethoxyethanol. Preferred solvents include ethyl lactate, propylene glycol methyl ether acetate, ethyl 3-ethoxypropionate and their mixtures. The above list of solvents is for illustrative purposes only and should not be viewed as being comprehensive nor should the choice of solvent be viewed as limiting the invention in any way.

Those skilled in the art will recognize that any number of solvents or solvent mixtures may be used.

Greater than 50 percent of the total mass of the resist formulation is typically composed of the solvent, preferably greater than 80 percent.

Other customary additives include dyes that may be used to adjust the optical density of the formulated resist and sensitizers which enhance the activity of photoacid generators by absorbing radiation and transferring it to the photoacid generator. Examples include aromatics such as functionalized benzenes, pyridines, pyrimidines, biphenylenes, indenes, naphthalenes, anthracenes, coumarins, anthraquinones, other aromatic ketones, and derivatives and analogs of any of the foregoing.

A wide variety of compounds with varying basicity may be used as stabilizers and acid-diffusion controlling additives. They may include nitrogenous compounds such as aliphatic primary, secondary, and tertiary amines, cyclic amines such as piperidines, pyrimidines, morpholines, aromatic heterocycles such as pyridines, pyrimidines, purines, imines such as diazabicycloundecene, guanidines, imides, amides, and others. Ammonium salts may also be used, including ammonium, primary, secondary, tertiary, and quaternary alkyl- and arylammonium salts of alkoxides including hydroxide, phenolates, carboxylates, aryl and alkyl sulfonates, sulfonamides, and others. Other cationic nitrogenous compounds including pyridinium salts and salts of other heterocyclic nitrogenous compounds with anions such as alkoxides including hydroxide, phenolates, carboxylates, aryl and alkyl sulfonates, sulfonamides, and the like may also be employed. Surfactants may be used to improve coating uniformity, and include a wide variety of ionic and non-ionic, monomeric, oligomeric, and polymeric species. Likewise, a wide variety of anti-foaming agents may be employed to suppress coating defects. Adhesion promoters may be used as well; again, a wide variety of compounds may be employed to serve this function. A wide variety of monomeric, oligomeric, and polymeric plasticizers such as oligo- and polyethyleneglycol ethers, cycloaliphatic esters, and non-acid reactive steroidally derived materials may be used as plasticizers, if desired. However, neither the classes of compounds nor the specific compounds mentioned above are intended to be comprehensive and/or limiting. One versed in the art will recognize the wide spectrum of commercially available products that may be used to carry out the types of functions that these customary additives perform.

Typically, the sum of all customary additives will comprise less than 20 percent of the solids included in the resist formulation, preferably, less than 5 percent.

The silsesquioxane photoresist compositions of the invention may also contain polymers selected to provide or increase transparency at a predetermined, desired wavelength, increase dry etch resistance, and/or improve aqueous base development. Representative such polymers are disclosed in published U.S. patent application 2003/0171490 A1 to Breyta et al., for "Polymer Blend and Associated Methods of Preparation and Use," assigned to International Business Machines Corporation. Preferred polymers are silicon-containing polymers and fluorinated polymers. Of the latter, preferred polymers contain monomer units bearing a fluoroalcohol group, such as NBHFA (bicyclo[2.2.1]hept-5-ene-2-(1,1,1-trifluoro-2-trifluoromethylpropan-2-ol).

These polymers may be NBHFA homopolymers ("PNB-HFA") or copolymers of NBHFA with other monomers, including, without limitation, other norbornene monomers.

IV. Use in Generation of Resist Images on a Substrate

The present invention also relates to a process for generating a resist image on a substrate. The process involves: (a) coating a substrate with a film of a photoresist composition provided herein; (b) pattern wise exposing the film to radiation; and (c) developing the image. The first step involves coating the substrate with a film comprising the resist composition dissolved in a suitable solvent. Suitable substrates are ceramic, metallic or semiconductive, and preferred substrates are silicon-containing, including, for example, silicon dioxide, silicon nitride, and silicon oxynitride. The substrate may or may not be coated with an organic anti-reflective layer prior to deposition of the resist composition. Alternatively, a bilayer resist may be employed wherein a resist composition provided herein forms an upper resist layer (i.e., the imaging layer), and the underlayer is comprised of a material that is highly absorbing at the imaging wavelength and compatible with the imaging layer. Any conventional underlayers, i.e., organic, polymeric, planarizing underlayers, may be used. Typically, it will be appreciated that these underlayers may be composed of hard-baked diazonaphthoquinone (DNQ)/novolak compositions, polyimides, polyesters, polyacrylates, or the like. DNQ novolac is the preferred polymer for the underlayer.

Preferably, the surface of the substrate is cleaned by standard procedures before the film is deposited thereon. Suitable solvents for the composition are as described in the preceding section, and include, for example, cyclohexanone, ethyl lactate, and propylene glycol methyl ether acetate. The film can be coated on the substrate using art-known techniques such as spin or spray coating, or doctor blading. Preferably, before the film has been exposed to radiation, the film is heated to a temperature of about 90–150° C., typically about 80–120° C., for a short period of time, typically on the order of about 1 minute. The dried film has a thickness of about 0.02 to 5.0 microns, preferably about 0.05 to 2.5 microns, and most preferably about 0.10 to 1.0 microns. The radiation may be ultraviolet, electron beam or x-ray. Ultraviolet radiation is preferred, particularly deep ultraviolet radiation having a wavelength of less than about 250 nm, e.g., 157 nm using an $F_2$ excimer laser. The radiation is absorbed by the radiation-sensitive acid generator to generate free acid, which with heating causes cleavage of the acid-labile pendant groups and formation of the corresponding acid. This "post-exposure bake" (PEB) process is carried out at a temperature below the $T_g$ of the silsesquioxane, which, as noted elsewhere herein, is greater than 50° C. Generally, PEB is carried out at a temperature at least 5° C. below $T_g$, more typically at a temperature at least 10° C. below $T_g$.

The third step involves development of the image with a suitable solvent. Suitable solvents include an aqueous base, preferably an aqueous base without metal ions such as the industry standard developer tetramethylammonium hydroxide or choline. Other solvents may include organic solvents or carbon dioxide (in the liquid or supercritical state), as disclosed in U.S. Pat. No. 6,665,527 to Allen et al. The the resist composition may be used with DUV wavelengths of 157 nm, 193 nm, or 248 nm, or with EUV (e.g., at 13 nm), electron beam or x-ray radiation.

The pattern from the resist structure may then be transferred to the material of the underlying substrate. Typically, the transfer is achieved by reactive ion etching or some other etching technique. Thus, the compositions provided herein and resulting resist structures can be used to create patterned material layer structures such as metal wiring lines, holes for contacts or vias, insulation sections (e.g., damascene trenches or shallow trench isolation), trenches for capacitor structures, etc. as might be used in the design of integrated circuit devices. Accordingly, the processes for making these features involves, after development with a suitable developer as above, etching the layer(s) underlying the resist layer at spaces in the pattern whereby a patterned material layer or substrate section is formed, and removing any remaining resist from the substrate. In some instances, a hard mask may be used below the resist layer to facilitate transfer of the pattern to a further underlying material layer or section. In the manufacture of integrated circuits, circuit patterns can be formed in the exposed areas after resist development by coating the substrate with a conductive material, e.g., a metallic material, using known techniques such as evaporation, sputtering, plating, chemical vapor deposition, or laser-induced deposition. Dielectric materials may also be deposited by similar means during the process of making circuits. Inorganic ions such as boron, phosphorous, or arsenic can be implanted in the substrate in the process for making p-doped or n-doped circuit transistors. Examples of such processes are disclosed in U.S. Pat. Nos. 4,855,017, 5,362,663, 5,429,710, 5,562,801, 5,618,751, 5,744,376, 5,801,094, and 5,821,469. Other examples of pattern transfer processes are described in Chapters 12 and 13 of Moreau, *Semiconductor Lithography, Principles, Practices, and Materials* (Plenum Press, 1988). It should be understood that the invention is not limited to any specific lithographic technique or device structure.

It is to be understood that while the invention has been described in conjunction with the preferred specific embodiments thereof, that the foregoing description as well as the examples that follow are intended to illustrate and not limit the scope of the invention. Other aspects, advantages and modifications within the scope of the invention will be apparent to those skilled in the art to which the invention pertains.

All patents, patent applications, and publications mentioned herein are hereby incorporated by reference in their entireties.

EXAMPLES

The following examples are intended to provide those of ordinary skill in the art with a complete disclosure and description of how to prepare and use the compositions disclosed and claimed herein. Efforts have been made to ensure accuracy with respect to numbers (e.g., amounts, temperature, etc.), but allowance should be made for the possibility of errors and deviations. Unless indicated otherwise, parts are parts by weight, temperature is in ° C. and pressure is at or near atmospheric. Additionally, all starting materials were obtained commercially or were synthesized using known procedures.

Where appropriate, the following techniques and equipment were utilized in the Examples: $^1$H and $^{13}$C NMR spectra were obtained at room temperature on an Avance 400 spectrometer. Quantitative $^{13}$C NMR was run at room temperature in acetone-$d_6$ in an inverse-gated $^1$H-decoupled mode using $Cr(acac)_3$ as a relaxation agent on an Avance 400 spectrometer. For polymer composition analysis $^{19}$F NMR (379 MHz) spectra were also obtained using a Bruker Avance 400 spectrometer. Thermo-gravimetric analysis (TGA) was performed at a heating rate of 5° C./min in $N_2$ on a TA Instrument Hi-Res TGA 2950 Thermogravimetric Analyzer. Differential scanning calorimetry (DSC) was performed at a heating rate of 10° C./min on a TA Instruments DSC 2920 modulated differential scanning calorimeter. Molecular weights were measured in tetrahydrofuran (THF) on a Waters Model 150 chromatograph relative to polystyrene standards. IR spectra were recorded on a Nicolet 510 FT-IR spectrometer on a film cast on a KBr plate. UV measurements at 157 nm were performed using a Varian Cary Model 400 spectrometer on multiple thickness on $CaF_2$ discs. Film thickness was measured on a Tencor alpha-step 2000. A quartz crystal microbalance (QCM) was used to study the dissolution kinetics of the resist films in an aqueous tetramethylammonium hydroxide (TMAH) solution (CD-26). Contact angles were measured on an AST Products VCA 2500XE video contact angle system using 2 μL of filtered deionized water.

The silesesquioxane starting materials were purchased from TAL Materials Inc., and Hybrid Plastics. Tetracyclo [4.4.0.1$^{2,5}$.1$^{7,12}$]dodec-3-ene starting materials were obtained from JSR corporation. All the other reagents were purchased from Aldrich Chemical Company. The products were characterized by NMR, IR, DSC, TGA, and GPC. The GPC traces of all the products showed a small shoulder on the high molecular weight side of the main peak. These are proposed to be dimers formed during the reaction (see Crivello et al. (1997), "Synthesis and Photoinitiated Polymerization of Monomers with the Silsesquioxane Core," *J. Polym. Sci., Part A: Polymer Chemistry* 35:407–425).

The nonpolymeric silsesquioxanes synthesized in the following examples have the general structure (1), (2), or (3) wherein R, $R^X$, and $R^Y$ are defined in each example.

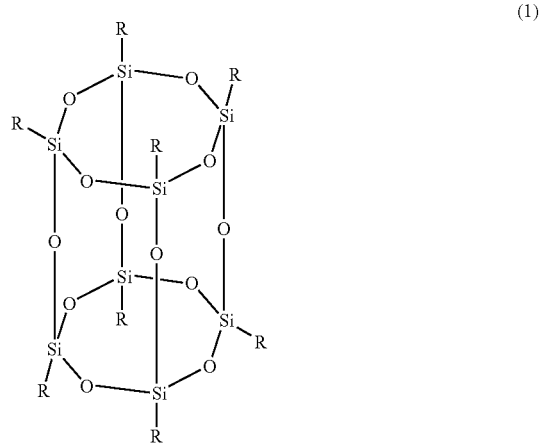

(1)

-continued (2)

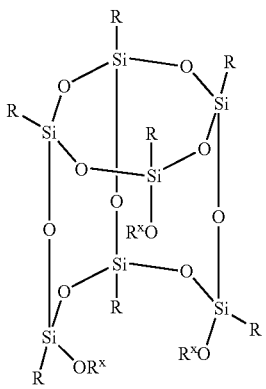

(3)

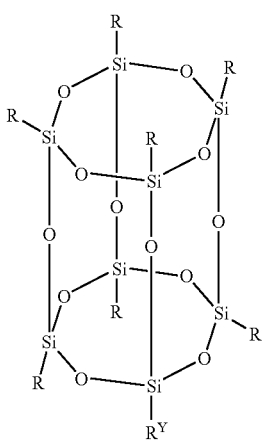

Example 1

Synthesis of Acid-Cleavable Compound 1A

Compound 1A, having the structure (1) wherein R is (1A-R)

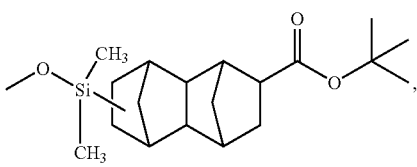

was synthesized as follows:

Octakis(dimethylsilyloxy)silsesquioxane $(Q_8M_8^H)$ (5.08 g, 0.005 mole), 2-tert-butyl tetracyclo[$4.4.0.1^{2,5}.1^{7,12}$]dodec-3-ene-5-carboxylate(TD-TBE) (11.44 g, 0.044 mole), and hexane (50 ml) were placed in a round bottom flask equipped with a magnetic stirrer, nitrogen inlet, and a water condensor. Platinum(0)-1,3-divinyl-1,1,3,3-tetramethyldisiloxane complex in xylene (1 ml) was added to this mixture and stirred at room temperature for 6 hours. Analysis of the IR spectrum of the reaction product indicated the reaction was complete. The solution was added dropwise into 500 ml methanol. The product coagulated and was rinsed twice with methanol (30 ml) and dried under vacuum at 70° C., yielding 8.07 g of final product.

Example 2

Synthesis of Acid-Cleavable Compound 1B

The method of Example 1 can be repeated using octakis (dimethylsilyloxy)-silsesquioxane $(Q_8M_8^H)$, 2-tetrahydropyranyl[$4.4.0.1^{2,5}.1^{7,12}$]dodec-3-ene-5-carboxylate to synthesize Compound 1B, having the structure (1) wherein R is (1B-R)

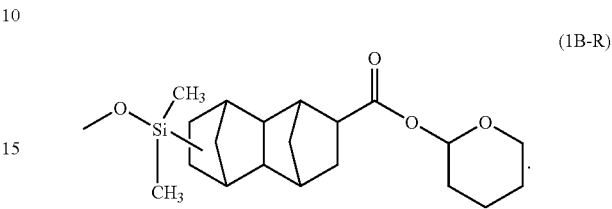

Example 3

Synthesis of Acid-Cleavable Compound 1C

Compound 1C, having the structure (1) wherein R is

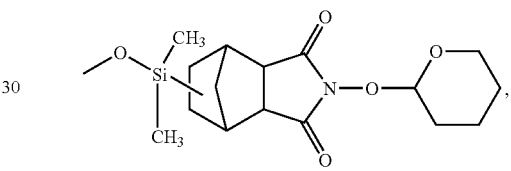

was synthesized as follows:

A. Synthesis of N-(2-Tetrahydro-2H-pyran-2-yloxy)-5-norbornene-2,3-dicarboximide:

To a 250 ml 3-neck round bottom flask equipped with condenser, thermometer, a nitrogen inlet and a magnetic stirrer bar was added N-Hydroxy-5-norbornene-2,3-dicarboximide (17.9 g, 0.10 mole), dihydropyran, (9.47 g, 0.11 mole) and 100 ml anhydrous THF. The mixture was stirred for ½ hour and a catalytic amount of triflouroacetic acid was added. The reaction solution was stirred at room temperature for 12 hours. Next, 10 g of basic $Al_2O_3$ was added and the mixture was stirred for 6 hours before filtration. A white solid was recovered following rotary evaporation of the solvent. The solid was dried in a vacuum oven at 50° C. overnight, yielding 99% final product. The identity of the product was analyzed with IR and $C^{13}$ NMR.

B. Synthesis of Compound 1C: To a 250 ml 3-neck round bottom flask equipped with a condenser, thermometer, nitrogen inlet and a magnetic stirring bar was added Octakis (dimethylsilyloxy)silsesquioxane $(Q_8M_8^H)$(5.08 g, 0.005 mole), endo-N-hydroxy-5-norbornene-2,3-dicarboximide tetrahydropyrene (11.79 g, 0.045 mole). The flask was transferred to an argon filled glove box and 150 ml dried THF (distilled on $CaH_2$) was transferred into the flask. The solid was not dissolved in THF at room temperature. Two shots of platinum(0)-1,3-divinyl-1,1,3,3-tetramethylsiloxane complex in xylene were added to the mixture (each shot was 0.75 ml of catayst/xylene solution). The flask was next transferred out of the glovebox and the reaction was conducted under $N_2$ flow at room temperature for 4 hours. The mixture turned to a milky slurry. The reaction mixture was heated at 67–70° C. and stirred for another four hours. IR analysis of the reaction solution indicated the disappearance of Si—H peak and the appearance of an imide bond. The reaction mixture was cooled to room temperature and added dropwise to stirred hexane (1:10). The slurry was stirred overnight before filtration. Following filtration, the solid was air-dried for a few hours before final drying overnight in a vacuum oven at 55° C. The final product yield was 73%.

Example 4

Synthesis of Acid-Cleavable Compound 1D

Compound 1D, having the structure (1) wherein four of the R groups are (1C—R) groups as in Example 3. and the remaining four R groups have the structure

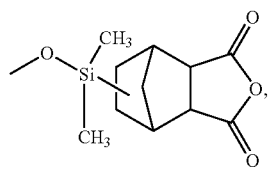
(1D-R)

was synthesized as follows:

A. Synthesis of 2-Tetrahydropyranyl tetracyclo[4.4.0.1$^{2,5}$.1$^{7,12}$]dodec-3-ene-5-carboxylate (TD-THP ester): Tetracyclo[4.4.0.1$^{2,5}$.1$^{7,12}$]dodec-3-ene-5-carboxic acid (TD-carboxylic acid) (6.12 g, 0.03 mole) and dihydropyran (5.04 g, 0.06 mole) were dissolved in 50 ml dichloromethane. Pyridinium p-toluenesulfonate (100 mg) was added to this solution and stirred at room temperature under nitrogen. After one hour, the solution was washed with 2×200 ml saturated sodium bicarbonate solution followed by 2×200 ml brine and was dried over anhydrous magnesium sulfate. The solvent was removed in a rotary evaporator and the product was used without further purification.

B. Synthesis of Compound ID: Octakis(dimethylsilyloxy) silsesquioxane ($Q_8M_8^H$) (5.08 g, 0.005 mole), cis-5-norbomene-endo-2,3-dicarboxylic anhydride (3.61 g, 0.022 mole), TD-THP ester (6.33 g, 0.022 mole) and anhydrous tetrahydrofuran (40 ml) were placed in a round bottom flask equipped with a magnetic stirrer, nitrogen inlet, and a water condenser. Platinum(0)-1,3-divinyl-1,1,3,3-tetramethyldisiloxane complex in xylene (2 ml) was added to this mixture and stirred at room temperature for 3 hours. Analysis of the IR spectrum of the reaction product indicated the reaction was not complete. The reaction solution was then heated to 50° C. for 2 hours. The solution was next allowed to cool to room temperature and added dropwise into 600 ml hexanes. Following coagulation, the product was rinsed twice with hexane (30 ml) and dried under vacuum at 50° C., yielding 12.30 g of final product.

Example 5

Synthesis of Acid-Cleavable Compound 1E

Compound 1E, having the structure (1) wherein R is

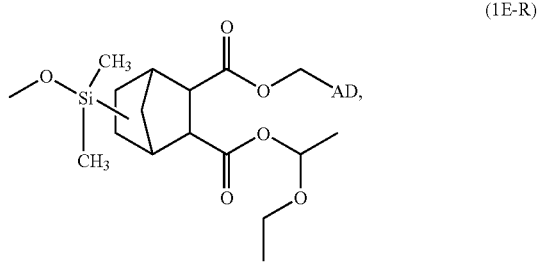
(1E-R)

(AD is adamantyl) was synthesized as follows:

A. Octa[(norbomane-2,3-dicarboxylic anhydride)dimethylsiloxy]silsesquioxane: Octakis(dimethylsilyloxy)silsesquioxane ($Q_8M_8^H$)(5.08 g, 0.005 mole), cis-5-norbomene-endo-2,3-dicarboxylic anhydride (7.22 g, 0.044 mole), and tetrahydrofuran (100 ml) were placed in a round bottom flask equipped with a magnetic stirrer, nitrogen inlet, and a water condenser. Platinum(0)-1,3-divinyl-1,1,3,3-tetramethyldisiloxane complex in xylene (1 ml) was added to this mixture and stirred at room temperature for 18 hours. Analysis of the IR spectrum of the reaction product indicated the reaction was not complete. It was then heated to reflux for 4 hours. The solution was allowed to cool to room temperature and added dropwise into 1.5 liter hexanes. The product coagulated and was rinsed twice with hexane (30 ml) and dried under vacuum at 80° C., yielding 5.60 g of final product.

B. Synthesis of octa[(norbornane-2-carboxylic acid-3-admantanemethylcarboxylate)-dimethylsiloxy]silsesquioxane: 1.74 g of octa[(norbornane-2,3-dicarboxylic anhydride) dimethylsiloxy]-silsesquioxane synthesized in A above and 0.996 g of 1-adamantanemethanol were dissolved in 13 g of tetrahydrofuran. Next, 0.76 g of dimethylamino pyridine was dissolved in 5 g of tetrahydrofliran and then slowly added to the solution. The reaction mixture was then refluxed at 72° C. for approximately 4 hours. The final solid product was precipitated out of 5% HCl solution and vacuum dried in vacuum oven at ~40° C. overnight.

C. Synthesis of Compound IE: 0.96 g of octa[(norbornane-2-carboxylicacid-3-admantanemethylcarboxylate)-dimethylsiloxy]silsesquioxane synthesized in B above was dissolved in 13 g of PGMEA. The solution was then combined with approximately 10 mg of trifluoracetic acid. Next, 0.6 g of ethylvinyl ether was added to the solution, and the reaction was carried out at room temperature with stirring overnight. The reaction was then quenched with 1.7 g of basic active aluminum oxide.

Example 6

Synthesis of Acid-Cleavable Compound 1F

Compound 1F, having the structure (1) wherein R is

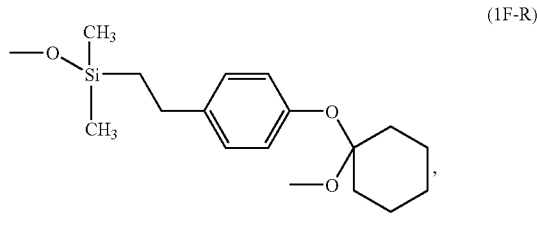

(1F-R)

was synthesized as follows:

A. Synthesis of Octa[(ethylphenol)dimethylsiloxy]silsesquioxane: 2 g of octa[(ethylphenylacetate)dimethylsiloxy]silsesquioxane was dissolved in 7.5 g of acetone. The solution was combined with 2.1 g of 3N HCl and refluxed at 60° C. for approximately 4 hours. The solid of octa[(ethylphenol)dimethylsiloxy]silsesquioxane was precipitated out of deionized water and dried in a vacuum oven at ~40° C. overnight. $C^{13}$ NMR showed that the compound was fully hydrolyzed to phenol end groups.

B. Synthesis of Compound IF: 0.9 g of octa[(ethylphenol)dimethylsiloxy]-silsesquioxane was dissolved in 10 g of PGMEA. The solution was then combined with approximately 2 mg of oxalic acid. After the acid was dissolved, 0.6 g of 1-methoxycyclohexene was added to the solution, and the reaction was carried out at room temperature with stirring overnight. NMR analysis showed only 46% protection. Another 0.6 g of 1-methoxycyclohexene was added to the reaction. After stirring for 3 days, the reaction was quenched with 2.2 g of basic active aluminum oxide. A protection level of 66% on phenol group was determined by $C^{13}$ NMR.

Example 7

Synthesis of Acid-Cleavable Compound 2A

Compound 2A, having the structure (2) wherein R is cyclopentyl and $R^X$ has the structure (1B—R), was synthesized as follows:

Endo-3,7,14-Tris(dimethylsilyloxy)-1,3,5,7,9,11,14-heptacyclopentyl-tricyclo[7.3.3.1$^{5,11}$] heptasiloxane (5.25 g, 0.005 mole), TD-THP ester (4.75 g, 0.0165 mole) a anhydrous tetrahydrofuran (40 ml) were placed in a round bottom flask equipped with a magnetic stirrer, nitrogen inlet, and a water condenser. Platinum(0)-1,3-divinyl-1,1,3,3-tetramethyl-disiloxane complex in xylene (1 ml) was added to this mixture and stirred at room temperature for 73 hours. Analysis of the IR spectrum of the reaction product indicated the reaction was not complete. It was then heated at 50° C. for 3 hours. The solution was allowed to cool to room temperature and added dropwise into a mixture of 400 ml DI water and 10 ml ammonium hydroxide. The product coagulated, and was rinsed twice with water (30 ml) and dried under vacuum at 50° C., yielding 8.2 g of a waxy solid.

Example 8

Synthesis of Acid-Cleavable Compound 3A

Compound 3A, having the structure (3) wherein R is isobutyl and $R^Y$ has the structure

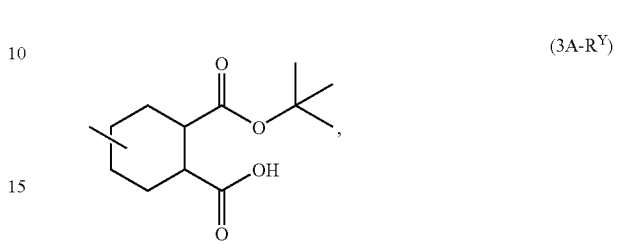

(3A-R$^Y$)

was synthesized as follows:

A. Synthesis of mono-tert-butyl-4-cyclohexene-1,2-dicarboxylate: This material was synthesized according to a procedure described in Guzzo et al. (1994), *J. Org. Chem.* 59:4862–4867, starting from tetrahydrophthalic anhydride.

B. Synthesis of Compound 3A: 1,3,5,7,9,11,13-Hepta(iso-butyl)pentacyclo-[9.5.1.1$^{3,9}$.1$^{5,15}$.1$^{7,13}$]-octasiloxane (8.18 g, 0.01 mole), mono-tert-butyl-4-cyclohexene-1,2-dicarboxylate (2.5 g, 0.011 mole) and tetrahydrofuran (40 ml) were placed in a round bottom flask equipped with a magnetic stirrer, nitrogen inlet, and a water condenser. Platinum(0)-1,3-divinyl-1,1,3,3-tetramethyldisiloxane complex in xylene (1 ml) was added to this mixture and heated to reflux for 4 hours. The solution was allowed to cool to room temperature and added dropwise into 1.5 liter deionized water. The product coagulated and was separated by decantation and dried under vacuum at 60° C. Next, the product was redissolved in 100 ml ether and stirred with 1 g of Amberlist-15 for 1 hour. The solution was filtered through celite and the solvent removed in a rotary evaporator. Drying of the product at 70° C. under vacuum for 18 hours yielded 8.3 g of waxy solid.

Example 9

Synthesis of Acid-Cleavable Compound 3B

The method of Example 8 can be repeated using mono-tert-butyl-4-bicyclo[2.2.1]heptene-1,2-dicarboxylate in place of mono-tert-butyl-4-cyclohexene-1,2-dicarboxylate to synthesize Compound 3A, having the structure (3) wherein $R^Y$ is

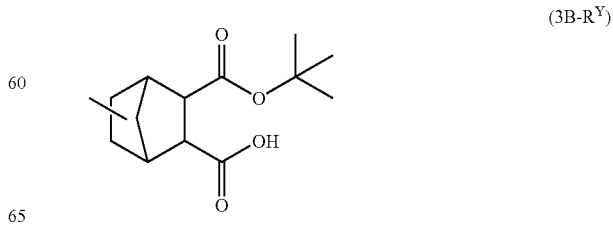

(3B-R$^Y$)

Example 10

Resist Formulation and Evaluation of Compound 1D at 193 nm

A mixture of compound 1D (1 g), triphenylsulfonium triflate (30 mg), tetrabutyl ammonium hydroxide (TBAH) (3 mg) and 400 ppm of FC-430 (surfactant, 3M) was dissolved in propylene glycol monomethyl ether acetate (6 g). The solution was filtered through a 0.2 micron syringe filter. A resist film was cast on a 5 inch silicon wafer at 3000 rpm and the film was baked at 90° C. for 1 minute. The film was exposed to 193 nm radiation using an Ultratech 0.65 NA stepper and was again baked at 50° C. for 1 minute. It was developed with 0.26 N TMAH solution for 30 seconds to give fine features (130 nm 1/s).

Example 11

E-Beam Evaluation of the Resist from Example 10

The resist formulation in Example 10 was spin coated at 3000 rpm on HMDS primed wafers. Next, the film was baked on a hot plate at 90° C. for 1 minute. Exposures were performed on a 100 kV Leica exposure system. After exposure, the resist was baked at 50° C. for 1 minute before developing with 0.263 N TMAH for 30 sec. High resolution of 50 nm 1/s images were resolved at 20–22 $\mu C/cm^2$ with resist lines standing, and 40 nm 1/s images were resolved with lines collapsed. 30 nm and 40 nm 1/s images were resolved at 18 $\mu C/cm^2$ with some residues between lines.

Example 12

Resist Formulation and E-Beam Evaluation of Compound 1E

Compound 1E with 0.15 wt. % (relative to the polymer) TBAH, 6 wt. % triphenylsulfonium triflate (TPS TRF), and 400 ppm of FC-430 surfactant were dissolved in PGMEA solvent. The total solid weight content in the solution was about 7.5%. The resist was spin coated on HMDS primed wafers. Next, the film was baked on a hot plate at 90° C. for 1 minute. The exposure was performed at 25 kV on an ElectronCure™-200M manufactured by Electron Vision Group. After exposure, the resist was baked at 70° C. for 1 minute and developed with 0.26 N TMAH for 60 seconds. The dose to clear was 32 $\mu C/cm$.

Example 13

Resist Formulation and E-Beam Evaluation of Compound 1C

A resist formulation was obtained by mixing compound 1C with 0.3 wt. % (relative to the polymer) TBAH, 3 wt. % TPS TRF, and 250 ppm of FC-430 surfactant in PGMEA solvent. The total solid weight content in the solution was about 8%. The resist was spin coated on HMDS primed wafer, and then was baked on a hot plate at 90° C. for 1 minute. The exposure was performed at 25 kV on Electron-Cure™-200M manufactured by Electron Vision Group. After exposure, the resist was baked at 50° C. for 1 minute and developed with 0.26N TMAH for 60 seconds. The dose to clear was 22 $mC/cm^2$.

We claim:

1. A nonpolymeric silsesquioxane in which at least one silicon atom is bound to at least one acid-cleavable alicyclic substituent $R^{CL}$, wherein the silsesquioxane has a glass transition temperature $T_g$ of greater than 50° C. and $R^{CL}$ is cleavable upon exposure to acid at a temperature below $T_g$, and further wherein the silsesquioxane is additionally substituted with at least one polar substituent $R^P$.

2. The silsesquioxane of claim 1, wherein $R^{CL}$ is cleavable upon exposure to acid at a temperature that is at least 5° C. below $T_g$.

3. The silsesquioxane of claim 1, selected from: (a) a polyhedral silsesquioxane optionally having one to three open vertices; and (b) a macromer of two to four polyhedral silsesquioxanes that may be the same or different, with each polyhedral silsesquioxane optionally having one to three open vertices.

4. The silsesquioxane of claim 3, wherein the polyhedral silsesquioxane of (a) and the polyhedral silsesquioxanes of (b) have from 4 to 10 faces.

5. The silsesquioxane of claim 1, wherein each silicon atom of the silsesquioxane is covalently bound to a moiety selected from: hydrogen; $R^{CL}$; an acid-inert, polar substituent $R^P$; and an acid-inert, nonpolar substituent $R^{NP}$.

6. The silsesquioxane of claim 1, wherein the silsesquioxane is additionally substituted with at least one non-polar substituent $R^{NP}$.

7. The silsesquioxane of claim 1, wherein $R^{CL}$ has the structure

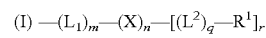

in which:

m and q are independently zero or 1;

n is 1;

r is an integer of at least 1;

$L^1$ is selected from —O—$SiR^2R^3$—, $C_1$–$C_{12}$ alkylene, substituted $C_1$–$C_{12}$ alkylene, $C_1$–$C12$ heteroalkylene, substituted $C_1$–$C_{12}$ heteroalkylene, $C_5$–$C_{14}$ arylene, substituted $C_5$–$C_{14}$ arylene, $C_5$–$C14$ heteroarylene, substituted $C_5$–$C_{14}$ heteroarylene, $C_6$–$C_{14}$ aralkylene, substituted $C_6$–$C_{14}$ aralkylene, $C_6$–$C_{14}$ heteroaralkylene, and substituted $C_6$–$C_{14}$ heteroaralkylene, wherein $R^2$ and $R^3$ are hydrogen or $C_1$–$C_{12}$ hydrocarbyl, and further wherein when $L^1$ is optionally substituted and/or heteroatom-containing $C_3$–$C_{12}$ alkylene, $L^1$ may be linear, branched, or cyclic;

X is selected from $C_3$–$C_{30}$ alicyclic and substituted $C_3$–$C_{30}$ alicyclic;

$L^2$ is selected from $C_1$–$C_{12}$ alkylene, substituted $C_1$–$C_{12}$ alkylene, $C_1$–$C_{12}$ heteroalkylene, substituted $C_1$–$C_{12}$ heteroalkylene, $C_5$–$C_{14}$ arylene, substituted $C_5$–$C_{14}$ arylene, $C_5$–$C_{14}$ heteroarylene, substituted $C_5$–$C_{14}$ heteroarylene, $C_6$–$C_{14}$ aralkylene, substituted $C_6$–$C_{14}$ aralkylene, $C_6$–$C_{14}$ heteroaralkylene, and substituted $C_6$–$C_{14}$ heteroaralkylene, and further wherein when $L^2$ is optionally substituted and/or heteroatom-containing $C_3$–$C_{12}$ alkylene, $L^2$ may be linear, branched, or cyclic; and $R^1$ is selected from acid-cleavable ester, oligomeric ester, ether, carbonate, acetal, ketal, and orthoester substituents.

8. The silsesquioxane of claim 7, wherein:

r is 1 or 2;

$L^1$ is selected from —O—$SiR^2R^3$— and $C_1$–$C_{12}$ alkylene;

$R^2$ and $R^3$ are hydrogen or $C_1$–$C_6$ hydrocarbyl;

X is $C_3$–$C_{18}$ alicyclic;

$L^2$ is selected from $C_1$–$C_{12}$ alkylene, hydroxyl-substituted $C_1$–$C_{12}$ alkylene, $C_1$–$C_{12}$ fluoroalkylene, and hydroxyl-substituted $C_1$–$C_{12}$ fluoroalkylene;

$R^1$ is selected from —(CO)—O—$R^4$, -[$Q^1$—(CO)—O—]$_h^4$, —O—$R^6$, and —O—(CO)—O—$R^7$;

h is an integer in the range of 2 to 8 inclusive;

$Q^1$ is $C_1$–$C_{12}$ alkylene or $C_1$–$C_{12}$ fluoroalkylene;

$R^4$ and $R^6$ are selected from (a) hydrocarbyl substituents with a tertiary carbon attachment point, (b) substituents having the structure —$CR^8R^9$—O—$CR^{10}R^{11}R^{12}$, and (c) substituents having the structure —$CR^{13}(OR^{14})_2$;

$R^5$, $R^7$, and $R^{14}$ are selected from $C_4$–$C_{12}$ hydrocarbyl, substituted $C_4$–$C_{12}$ hydrocarbyl, heteroatom-containing $C_4$–$C_{12}$ hydrocarbyl, and substituted heteroatom-containing $C_4$–$C_{12}$ hydrocarbyl; and $R^8$, $R^9$, $R^{10}$, $R^{11}$, $R^{12}$, $R^{13}$ are independently selected from hydrogen, $C_4$–$C_{12}$ hydrocarbyl, substituted $C_4$–$C_{12}$ hydrocarbyl, heteroatom-containing $C_4$–$C_{12}$ hydrocarbyl, and substituted heteroatom-containing $C_4$–$C_{12}$ hydrocarbyl, and further wherein any two of $R^8$, $R^9$, $R^{10}$, $R^{11}$, and $R^{12}$ may be linked to form a three- to eight-membered cyclic group.

9. The silsesquioxane of claim 8, wherein:

$L^1$ is selected from —O—$SiR^2R^3$— and $C_1$–$C_6$ alkylene;

$R^2$ and $R^3$ are hydrogen or $C_1$–$C_6$ alkyl;

X is $C_6$–$C_{12}$ alicyclic; and $L^2$ is of the formula —$CR^{15}R^{16}$— wherein $R^{15}$ is hydrogen, $C_1$–$C_{12}$ alkyl, or $C_1$–$C_{12}$ fluoroalkyl, and $R^{16}$ is $C_1$–$C_{12}$ alkyl or $C_1$–$C_{12}$ fluoroalkyl.

10. The silsesquioxane of claim 9, wherein:

$R^1$ is of the formula —(CO)—O—$R^4$, wherein $R^4$ is selected from cyclic and acyclic hydrocarbyl substituents with a tertiary carbon attachment point, such that when r is 1, then $R^{CL}$ has the structure (II) —($L^1$)$_m$—(X)$_n$—($CR^{15}R^{16}$)$_q$—(CO)—O—$R^4$ 11. The silsesquioxane of claim 9, wherein:

$R^1$ is of the formula —O—$R^6$, wherein $R^6$ is selected from cyclic and acyclic hydrocarbyl substituents with a tertiary carbon attachment point, such that when r is 1, then $R^{CL}$ has the structure (III) —($L^1$)$_m$—(X)$_n$—($CR^{15}R^{16}$)$_q$—O—$R^6$.

12. The silsesquioxane of claim 10, wherein $R^4$ is selected from t-butyl, adamantyl, norbornyl, isobornyl, 2-methyl-2-adamantyl, 2-methyl-2-isobornyl, 2-methyl-2-tetracyclododecenyl, 2-methyl-2-dihydrodicyclo-pentadienyl-cyclohexyl, 1-methylcyclohexyl, 1-methylcyclopentyl, 1-methylcyclopentyl, tetrahydropyranyl (THP), tetrahydrofuranyl (THF), 1-ethoxyethyl, 1-methoxy-cyclohexyl, and 1-methoxypropyl.

13. The silsesquioxane of claim 11, wherein $R^6$ is selected from t-butyl, adamantyl, norbornyl, isobornyl, 2-methyl-2-adamantyl, 2-methyl-2-isobornyl, 2-methyl-2-tetracyclododecenyl, 2-methyl-2-dihydrodicyclo-pentadienyl-cyclohexyl, 1-methylcyclohexyl, 1-methylcyclopentyl, tetrahydropyranyl (THP), tetrahydrofuranyl (THF), 1-ethoxyethyl, 1-methoxy-cyclohexyl, and 1-methoxypropyl.

14. The silsesquioxane of claim 1, wherein $R^P$ has the structure

-($L^3$)$_{m1}$-(Y)$_{n1}$-($L^4$)$_{q1}$-$R^{18}$ (IV)

in which:

m1, n1, and q1 are independently zero or 1;

$L^3$ is selected from —O—$SiR^{19}R^{20}$—, $C_1$–$C_{12}$ alkylene, substituted $C_1$–$C_{12}$ alkylene, $C_1$–C12 heteroalkylene, substituted $C_1$–$C_{12}$ heteroalkylene, $C_5$–$C_{14}$ arylene, substituted $C_5$–$C_{14}$ arylene, $C_5$–$C_{14}$ heteroarylene, substituted $C_5$–$C_{14}$ heteroarylene, $C_6$–$C_{14}$ aralkylene, substituted $C_6$–$C_{14}$ aralkylene, $C_6$–$C_{14}$ heteroaralkylene, and substituted $C_6$–$C_{14}$ heteroaralkylene, wherein $R^{19}$ and $R^{20}$ are hydrogen or $C_1$–$C_{12}$ hydrocarbyl, and further wherein when $L^3$ is optionally substituted and/or heteroatom-containing $C_3$–C12 alkylene, $L^1$ may be linear, branched, or cyclic;

Y is selected from $C_3$–$C_{30}$ alicyclic and substituted $C_3$–$C_{30}$ alicyclic;

$L^4$ is selected from $C_1$–$C_{12}$ alkylene, substituted $C_1$–$C_{12}$ alkylene, $C_1$–$C_{12}$ heteroalkylene, substituted $C_1$–$C_{12}$ heteroalkylene, $C_5$–$C_{14}$ arylene, substituted $C_5$–$C_{14}$ arylene, $C_5$–$C_{14}$ heteroarylene, substituted $C_5$–$C_{14}$ heteroarylene, $C_6$–$C_{14}$ aralkylene, substituted $C_6$–$C_{14}$ aralkylene, $C_6$–C14 heteroaralkylene, and substituted $C_6$–$C_{14}$ heteroaralkylene, and further wherein when $L^4$ is optionally substituted and/or heteroatom-containing $C_3$–$C_{12}$ alkylene, $L^4$ may be linear, branched, or cyclic; and $R^{18}$ is an acid-inert polar organic group containing a heteroatom with a Pauling electronegativity greater than about 3.00.

15. The silsesquioxane of claim 14, wherein:

$L^3$ is selected from —O—$SiR^{19}R^{20}$— and $C_1$–$C_{12}$ alkylene;

Y is $C_3$–$C_{18}$ alicyclic; and $L^4$ is selected from $C_1$–$C_{12}$ alkylene, hydroxyl-substituted $C_1$–$C_{12}$ alkylene, $C_1$–$C_{12}$ fluoroalkylene, and hydroxyl-substituted $C_1$–$C_{12}$ fluoroalkylene.

16. The silsesquioxane of claim 15, wherein:

$L^3$ is selected from —O—$SiR^{19}R^{20}$— and $C_1$–$C_6$ alkylene;

Y is $C_6$–$C_{12}$ alicyclic; and $L^4$ is of the formula —$CR^{21}CR^{22}$— wherein $R^{21}$ is hydrogen, $C_1$–$C_{12}$ alkyl, or $C_1$–$C_{12}$ fluoroalkyl, and $R^{22}$ is $C_1$–$C_{12}$ alkyl or $C_1$–$C_{12}$ fluoroalkyl, such that $R^P$ has the structure —($L^3$)$_{m1}$-(Y)$_{n1}$—($CR^{21}R^{22}$)$_{q1}$—$R^{18}$. (V)

17. The silsesquioxane of claim 16, wherein the heteroatom within $R^{18}$ is O or N.

18. The silsesquioxane of claim 17, wherein $R^{18}$ is selected from hydroxyl, carboxyl, $C_1$–$C_{12}$ alkoxy, $C_1$–$C_{12}$ fluoroalkoxy, hydroxyl-substituted $C_1$–$C_{12}$ alkoxy, hydroxyl-substituted $C_1$–C12 fluoroalkoxy, $C_2$–$C_{12}$ alkoxyalkyl, fluorinated $C_2$–$C_{12}$ alkoxyalkyl, hydroxyl-substituted $C_2$–$C_{12}$ alkoxyalkyl, fluorinated hydroxyl-substituted $C_2$–$C_{12}$ alkoxyalkyl, hydroxyl-substituted $C_1$–$C_{12}$ alkyl, hydroxyl-substituted $C_1$–$C_{12}$ fluoroalkyl, carboxyl-substituted $C_1$–$C_{12}$ alkyl, carboxyl-substituted $C_1$–$C_{12}$ fluoroalkyl, $C_2$–$C_{12}$ acyl, fluorinated $C_2$–$C_{12}$ acyl, $C_2$–$C_{12}$ acyl, fluorinated hydroxyl-substituted $C_2$–$C_{12}$ acyl, $C_2$–$C_{12}$ acyloxy, fluorinated $C_2$–$C_{12}$ acyloxy, hydroxyl-substituted $C_2$–C12 fluorinated hydroxyl-substituted $C_2$–$C_{12}$ acyloxy, amino, mono- and di-($C_1$–$C_{12}$ alkyl)-substituted amino, amido, mono- and di-($C_2$–$C_{12}$ alkyl)amido, sulfonamido, N-heteroalicyclic, oxo-substituted N-heterocyclic, and, where the substituents permit, combinations of two or more of the foregoing.

19. The silsesquioxane of claim 18, wherein $R^{18}$ is hydroxyl.

20. The silsesquioxane of claim 17, wherein n1 is 1.

21. The silsesquioxane of claim 20, wherein q1 is zero.

22. The silsesquioxane of claim 6, wherein $R^{NP}$ is $C_1$–C18 hydrocarbyl or fluorinated $C_1$–$C_{18}$ hydrocarbyl.

23. A lithographic photoresist composition comprising a photoacid generator and a nonpolymeric silsesquioxane in which at least one silicon atom is bound to at least one acid-cleavable alicyclic substituent $R^{CL}$, wherein the silsesquioxane has a glass transition temperature $T_g$ of greater than 50° C. and $R^{CL}$ is cleavable upon exposure to acid at a temperature below $T_g$ and further wherein the silsesquioxane is additionally substituted with at least one polar substituent $R^P$.

24. The composition of claim 23, wherein $R^{CL}$ is cleavable upon exposure to acid at a temperature that is at least 5° C. below $T_g$.

25. The composition of claim 23, selected from: (a) a polyhedral silsesquioxane optionally having one to three open vertices; and (b) a macromer of two to four polyhedral silsesquioxanes that may be the same or different, with each polyhedral silsesquioxane optionally having one to three open vertices.

26. The composition of claim 25, wherein the polyhedral silsesquioxane of (a) and the polyhedral silsesquioxanes of (b) have from 4 to 10 faces.

27. The composition of claim 23, wherein each silicon atom of the silsesquioxane is covalently bound to a moiety selected from: hydrogen; $R^{CL}$; an acid-inert, polar substituent $R^P$; and an acid-inert, nonpolar substituent $R^{NP}$.

28. The composition of claim 23, wherein the silsesquioxane is additionally substituted with at least one non-polar substituent $R^{NP}$.

29. The composition of claim 23, wherein $R^{CL}$ has the structure

in which:
m and q are independently zero or 1;
n is 1;
r is an integer of at least 1;
$L^1$ is selected from —O—SiR²R³—, $C_1$–$C_{12}$ alkylene, substituted $C_1$–$C_{12}$ alkylene, $C_1$–C12 heteroalkylene, substituted $C_1$–$C_{12}$ heteroalkylene, $C_5$–$C_{14}$ arylene, substituted $C_5$–$C_{14}$ arylene, $C_5$–$C_{14}$ heteroarylene, substituted $C_5$–$C_{14}$ heteroarylene, $C_6$–$C_{14}$ aralkylene, substituted $C_6$–$C_{14}$ aralkylene, $C_6$–$C_{14}$ heteroaralkylene, and substituted $C_6$–$C_{14}$ heteroaralkylene, wherein $R^2$ and $R^3$ are hydrogen or $C_1$–$C_{12}$ hydrocarbyl, and further wherein when $L^1$ is optionally substituted and/or heteroatom-containing $C_3$–C12 alkylene, $L^1$ may be linear, branched, or cyclic;
X is selected from $C_3$–$C_{30}$ alicyclic and substituted $C_3$–$C_{30}$ alicyclic;
$L^2$ is selected from $C_1$–$C_{12}$ alkylene, substituted $C_1$–$C_{12}$ alkylene, $C_1$–$C_{12}$ heteroalkylene, substituted $C_1$–$C_{12}$ heteroalkylene, $C_5$–$C_{14}$ arylene, substituted $C_5$–$C_{14}$ arylene, $C_5$–$C_{14}$ heteroarylene, substituted $C_5$–$C_{14}$ heteroarylene, $C_6$–$C_{14}$ aralkylene, substituted $C_6$–$C_{14}$ aralkylene, $C_6$–C14 heteroaralkylene, and substituted $C_6$–$C_{14}$ heteroaralkylene, and further wherein when $L^2$ is optionally substituted and/or heteroatom-containing $C_3$–$C_{12}$ alkylene, $L^2$ may be linear, branched, or cyclic; and
$R^1$ is selected from acid-cleavable ester, oligomeric ester, ether, carbonate, acetal, ketal, and orthoester substituents.

30. The composition of claim 29, wherein:
r is 1 or 2;
$L^1$ is selected from —O—SiR²R³— and $C_1$–$C_{12}$ alkylene;
$R^2$ and $R^3$ are hydrogen or $C_1$–$C_6$ hydrocarbyl;
X is $C_3$–$C_{18}$ alicyclic;
$L^2$ is selected from $C_1$–$C_{12}$ alkylene, hydroxyl-substituted $C_1$–$C_{12}$ alkylene, $C_1$–$C_{12}$ fluoroalkylene, and hydroxyl-substituted $C_1$–$C_{12}$ fluoroalkylene; and
$R^1$ is selected from —(CO)—O—$R^4$, -[$Q^1$—(CO)—O—] h-$R^5$, —O—$R^6$, and —O—(CO)—O—$R^7$;
h is an integer in the range of 2 to 8 inclusive,
$Q^1$ is $C_1$–$C_{12}$ alkylene or $C_1$–$C_{12}$ fluoroalkylene,
$R^4$ and $R^6$ are selected from (a) hydrocarbyl substituents with a tertiary carbon attachment point, (b) substituents having the structure —CR⁸R⁹—O—CR¹⁰R¹¹R¹², and (c) substituents having the structure —CR¹³(OR¹⁴)₂;
$R^5$, $R^7$, and $R^{14}$ are selected from $C_4$–$C_{12}$ hydrocarbyl, substituted $C_4$–$C_{12}$ hydrocarbyl, heteroatom-containing $C_4$–$C_{12}$ hydrocarbyl, and substituted heteroatom-containing $C_4$–$C_{12}$ hydrocarbyl; and
$R^8$, $R^9$, $R^{10}$, $R^{11}$, $R^{12}$, and $R^{13}$ are independently selected from hydrogen, $C_4$–$C_{12}$ hydrocarbyl, substituted $C_4$–$C_{12}$ hydrocarbyl, heteroatom-containing $C_4$–$C_{12}$ hydrocarbyl, and substituted heteroatom-containing $C_4$–$C_{12}$ hydrocarbyl, and further wherein any two of $R^8$, $R^9$, $R^{10}$, $R^{11}$, and $R^{12}$ may form a three- to eight-membered cyclic group.

31. The composition of claim 30, wherein:
$L^1$ is selected from —O—SiR²R³— and $C_1$–$C_6$ alkylene;
$R^2$ and $R^3$ are hydrogen or $C_1$–$C_6$ alkyl;
X is $C_6$–$C_{12}$ alicyclic; and
$L^2$ is of the formula —CR¹⁵R¹⁶— wherein $R^{15}$ is hydrogen, $C_1$–$C_{12}$ alkyl, or $C_1$–$C_{12}$ fluoroalkyl, and $R^{16}$ is $C_1$–$C_{12}$ alkyl or $C_1$–$C_{12}$ fluoroalkyl.

32. The composition of claim 31, wherein $R^1$ is of the formula —(CO)—O—$R^4$, wherein $R^4$ is selected from cyclic and acyclic hydrocarbyl substituents with a tertiary carbon attachment point, such that when r is 1, then $R^{CL}$ has the structure

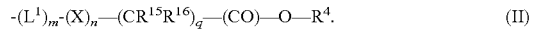

33. The composition of claim 31, wherein is of the formula —O—$R^6$, wherein $R^6$ is selected from cyclic and acyclic hydrocarbyl substituents with a tertiary carbon attachment point, such that when r is 1, then $R^{CL}$ as the structure

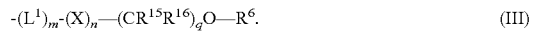

34. The composition of claim 32, wherein $R^4$ is selected from t-butyl, adamantyl, norbornyl, isobornyl, 2-methyl-2-adamantyl, 2-methyl-2-isobornyl, 2-methyl-2-tetracyclododecenyl, 2-methyl-2-dihydrodicyclo-pentadienyl-cyclohexyl, 1-methylcyclohexyl, 1-methylcyclopentyl, tetrahydropyranyl (THP), tetrahydrofuranyl (THF), 1-ethoxyethyl, 1-methoxy-cyclohexyl, and 1-methoxypropyl.

35. The composition of claim 32, wherein is selected from t-butyl, adamantyl, norbornyl, isobornyl, 2-methyl-2-adamantyl, 2-methyl-2-isobornyl, 2-methyl-2-tetracyclododecenyl, 2-methyl-2-dihydrodicyclo-pentadienyl-cyclohexyl, 1-methylcyclohexyl, 1-methylcyclopentyl, tetrahydropyranyl (THP), tetrahydrofuranyl (THF), 1-ethoxyethyl, 1-methoxy-cyclohexyl, and 1-methoxypropyl.

36. The composition of claim 23, wherein $R^P$ has the structure

in which:
m1, n1, and q1 are independently zero or 1;
$L^3$ is selected from —O—SiR¹⁹R²⁰-, $C_1$–$C_{12}$ alkylene, substituted $C_1$–$C_{12}$ alkylene, $C_1$–C12 heteroalkylene, substituted $C_1$–$C_{12}$ heteroalkylene, $C_5$–$C_{14}$ arylene, substituted $C_5$–$C_{14}$ arylene, $C_5$–$C_{14}$ heteroarylene, substituted $C_5$–$C_{14}$ heteroarylene, $C_6$–$C_{14}$ aralkylene, substituted $C_6$–$C_{14}$ aralkylene, $C_6$–$C_{14}$ heteroaralkylene, and substituted $C_6$–$C_{14}$ heteroaralkylene, wherein $R^{19}$ and $R^{20}$ are hydrogen or $C_1$–$C_{12}$ hydrocarbyl, and further wherein when $L^3$ is optionally substituted and/or heteroatom-containing $C_3$–$C_{12}$ alkylene, $L^1$ may be linear, branched, or cyclic;

Y is selected from $C_3$–$C_{30}$ alicyclic and substituted $C_3$–$C_{30}$ alicyclic;

$L^4$ is selected from $C_1$–$C_{12}$ alkylene, substituted $C_1$–$C_{12}$ alkylene, $C_1$–$C_{12}$ heteroalkylene, substituted $C_1$–$C_{12}$ heteroalkylene, $C_5$–$C_{14}$ arylene, substituted $C_5$–$C_{14}$ arylene, $C_5$–$C_{14}$ heteroarylene, substituted $C_5$–$C_{14}$ heteroarylene, $C_6$–$C_{14}$ aralkylene, substituted $C_6$–$C_{14}$ aralkylene, $C_6$–$C_{14}$ heteroaralkylene, and substituted $C_6$–$C_{14}$ heteroaralkylene, and further wherein when $L^4$ is optionally substituted and/or heteroatom-containing $C_3$–$C_{12}$ alkylene, $L^4$ may be linear, branched, or cyclic; and $R^{18}$ is an acid-inert polar organic group containing a heteroatom with a Pauling electronegativity greater than about 3.00.

37. The composition of claim 36, wherein:

$L^3$ is selected from —O—$SiR^{19}R^{20}$— and $C_1$–$C_{12}$ alkylene;

Y is $C_3$–$C_{18}$ alicyclic; and $L^4$ is selected from $C_1$–$C_{12}$ alkylene, hydroxyl-substituted $C_1$–$C_{12}$ alkylene, $C_1$–$C_{12}$ fluoroalkylene, and hydroxyl-substituted $C_1$–$C_{12}$ fluoroalkylene.

38. The composition of claim 37, wherein:

$L^3$ is selected from —O—$SiR^{19}R^{20}$— and $C_1$–$C_6$ alkylene;

Y is $C_6$–$C_{12}$ alicyclic; and $L^4$ is of the formula —$CR^{21}CR^{22}$— wherein $R^{21}$ is hydrogen, $C_1$–$C_{12}$ alkyl, or $C_1$–$C_{12}$ fluoroalkyl, and $R^{22}$ is $C_1$–$C_{12}$ alkyl or $C_1$–$C_{12}$ fluoroalkyl, such that $R^P$ has the structure

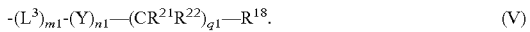

$$-(L^3)_{m1}-(Y)_{n1}-(CR^{21}R^{22})_{q1}-R^{18}. \qquad (V)$$

39. The composition of claim 38, wherein the heteroatom within $R^{18}$ is O or N.

40. The composition of claim 39, wherein $R^{18}$ is selected from hydroxyl, carboxyl, $C_1$–$C_{12}$ alkoxy, $C_1$–$C_{12}$ fluoroalkoxy, hydroxyl-substituted $C_1$–$C_{12}$ alkoxy, hydroxyl-substituted $C_1$–$C_{12}$ fluoroalkoxy, $C_2$–$C_{12}$ alkoxyalkyl, fluorinated $C_2$–$C_{12}$ alkoxyalkyl, hydroxyl-substituted $C_2$–$C_{12}$ alkoxyalkyl, fluorinated hydroxyl-substituted $C_2$–$C_{12}$ alkoxyalkyl, hydroxyl-substituted $C_1$–$C_{12}$ alkyl, hydroxyl-substituted $C_1$–$C_{12}$ fluoroalkyl, carboxyl-substituted $C_1$–$C_{12}$ alkyl, carboxyl-substituted $C_1$–$C_{12}$ fluoroalkyl, $C_2$–$C_{12}$ acyl, fluorinated $C_2$–$C_{12}$ acyl, hydroxyl-substituted $C_2$–$C_{12}$ acyl, fluorinated hydroxyl-substituted $C_2$–$C_{12}$ acyl, $C_2$–$C_{12}$ acyloxy, fluorinated $C_2$–$C_{12}$ acyloxy, hydroxyl-substituted $C_2$–$C_{12}$ acyloxy, fluorinated hydroxyl-substituted $C_2$–$C_{12}$ acyloxy, amino, mono- and di-($C_1$–$C_{12}$ alkyl)-substituted amino, amido, mono- and di-($C_2$–$C_{12}$ alkyl)amido, sulfonamido, N-heteroalicyclic, oxo-substituted N-heterocyclic, and, where the substituents permit, combinations of two or more of the foregoing.

41. The composition of claim 40, wherein $R^{18}$ is hydroxyl.

42. The composition of claim 39, wherein n1 is 1.

43. The composition of claim 42, wherein q1 is zero.

44. The composition of claim 28, wherein $R^{NP}$ is $C_1$–$C_{18}$ hydrocarbyl or fluorinated $C_1$–$C_{18}$ hydrocarbyl.

45. The composition of claim 23, further comprising a dissolution modifying additive.

46. The composition of claim 45, wherein the dissolution modifying additive is a dissolution inhibitor.

47. The composition of claim 23, further comprising a polymer selected to provide transparency at a predetermined wavelength.

48. The composition of claim 47, wherein the polymer is selected from silicon-containing polymers and fluorinated polymers.

49. The composition of claim 23, further comprising a solvent.

50. The composition of claim 23, wherein the photoacid generator is an onium salt selected from sulfonium salts and iodonium salts.

51. A process for patterning a substrate, comprising:

(a) coating a substrate with a photoresist composition comprised of (i) a nonpolymeric silsesquioxane in which at least one silicon atom is bound to an acid-cleavable substituent $R^{CL}$, wherein the silsesquioxane has a glass transition temperature $T_g$ of greater than 50° C., and (ii) a photoacid generator, thereby forming a film;

(b) baking the coated substrate at a post-application bake temperature in the range of about 90° C. to about 150° C.;

(c) patternwise exposing the film to an imaging radiation source so as to form a latent, patterned image in the film;

(d) baking the exposed film at a post-exposure bake temperature below $T_g$; and (e) developing the latent image with a developer to form a patterned substrate.

52. The process of claim 51, wherein the nonpolymeric silsesquioxane is selected from: (a) a polyhedral silsesquioxane optionally having one to three open vertices; and (b) a macromer of two to four polyhedral silsesquioxanes that may be the same or different, with each polyhedral silsesquioxane optionally having one to three open vertices.

53. The process of claim 51, wherein the post-exposure bake temperature is at least 5° C. below $T_g$.

54. The process of claim 53, wherein the post-exposure bake temperature is at least 10° C. below $T_g$.

55. The process of claim 54, further including, in step (b), baking the coated substrate at a post-application bake temperature in the range of about 80° C. to about 120° C.

56. The process of claim 51, wherein the radiation is electron-beam, x-ray, ultraviolet, or extreme ultraviolet radiation.

57. The process of claim 56, wherein the radiation is ultraviolet radiation.

58. The process of claim 57, wherein the ultraviolet radiation has a wavelength of 248 nm, 193 nm, 157 nm, or 13.4 nm.

59. The process of claim 58, wherein the ultraviolet radiation has a wavelength of 193 nm.

60. The process of claim 51, further comprising etching the patterned substrate.

61. The process of claim 60, wherein the etching comprises ion etching.

62. The process of claim 51, wherein the film is insoluble, and wherein the developer renders the film soluble where exposed to the imaging radiation source.

63. The process of claim 62, further comprising removing the soluble film.

64. The process of claim 51, wherein the substrate comprises a silicon wafer, a photolithographic mask blank, or a printed circuit board.

65. The process of claim 51, wherein the substrate coated in (a) has a surface layer of an organic material, such that the patterned substrate is composed of a patterned bilayer resist having an underlayer of the organic material.

66. The process of claim 65, wherein the organic material is selected from diazonaphthoquinone/novolac, polyimides, polyesters, and polyacrylates.

67. The patterned substrate prepared by the process of claim 51.

68. The silsesquioxane of claim 2, wherein $R^{CL}$ is cleavable upon exposure to acid at a temperature that is at least 10° C. below $T_g$.

69. The composition of claim 24, wherein $R^{CL}$ is cleavable upon exposure to acid at a temperature that is at least 10° C. below $T_g$.

* * * * *

UNITED STATES PATENT AND TRADEMARK OFFICE
CERTIFICATE OF CORRECTION

PATENT NO. : 7,141,692 B2
APPLICATION NO. : 10/721302
DATED : November 28, 2006
INVENTOR(S) : Robert David Allen et al.

It is certified that error appears in the above-identified patent and that said Letters Patent is hereby corrected as shown below:

Claim 8 (col. 27, line 5): the formula "-$[Q^1\text{-}(CO)\text{-}O\text{-}]_h^4$" should be -- -$[Q^1\text{-}(CO)\text{-}O\text{-}]_h\text{-}R^5$--;

Claim 12 (col. 27, line 49): the second instance of "1-methylcyclopentyl" should be deleted;

Claim 14 (col. 27, line 67): the term "C12" should be --$C_{12}$--;

Claim 14 (col. 28, line 8): the term "C12" should be --$C_{12}$--;

Claim 14 (col. 28, line 17): the term "C14" should be --$C_{14}$--;

Claim 18 (col. 28, line 47): the term "C12" should be --$C_{12}$--;

Claim 18 (col. 28, line 56): the term "C12" should be --$C_{12}$--;

Claim 22 (col. 28, line 66): the term "C18" should be --$C_{18}$--;

Claim 23 (col. 29, line 6): the term "50° C." should be --50°C--;

Claim 24 (col. 29, line 12:) the term "5° C." should be --5°C--;

Claim 29 (col. 29, line 38): the term "C12" should be --$C_{12}$--;

Claim 29 (col. 29, line 46): the term "C12" should be --$C_{12}$--;

Claim 29 (col. 29, line 55): the term "C14" should be --$C_{14}$--;

Claim 30 (col. 30, line 5): the formula "-$[Q^1\text{-}(CO)\text{-}O\text{-}]h\text{-}R^5$" should be -- -$[Q^1\text{-}(CO)\text{-}O\text{-}]_h\text{-}R^5$--;

Claim 30 (col. 30, lines 21-22): the phrase "may form a three- to eight-membered cyclic group" should be -- may be linked to form a three- to eight-membered cyclic group--;

Claim 35 (col. 30, line 52): the phrase "The composition of claim 32, wherein is selected from" should be --The composition of claim 32, wherein $R^6$ is selected from--;

Claim 36 (col. 30, line 66): the term "C12" should be --$C_{12}$--;

UNITED STATES PATENT AND TRADEMARK OFFICE
CERTIFICATE OF CORRECTION

PATENT NO. : 7,141,692 B2
APPLICATION NO. : 10/721302
DATED : November 28, 2006
INVENTOR(S) : Robert David Allen et al.

It is certified that error appears in the above-identified patent and that said Letters Patent is hereby corrected as shown below:

Claim 51 (col. 32, line 20):   the term "50° C." should be --50°C--;

Claim 51 (col. 32, line 23):   the term "90° C." should be --90°C--;

Claim 51 (col. 32, lines 23-24): the term "150° C." should be --150°C--;

Claim 53 (col. 32, line 39):   the term "5° C." should be --5°C--;

Claim 54 (col. 32, line 41):   the term "10° C." should be --10°C--; and

Claim 55(col. 32, line 45):    the term "80° C." should be --80°C--.

Signed and Sealed this

Twenty-seventh Day of March, 2007

JON W. DUDAS
*Director of the United States Patent and Trademark Office*